US012685724B2

(12) United States Patent
Ben Assayag

(10) Patent No.: US 12,685,724 B2
(45) Date of Patent: Jul. 21, 2026

(54) ANTIDEPRESSANT THERAPY

(71) Applicant: ICHILOV TECH LTD., Tel Aviv (IL)

(72) Inventor: Einor Ben Assayag, Shoham (IL)

(73) Assignee: ICHILOV TECH LTD., Tel Aviv (IL)

( * ) Notice: Subject to any disclaimer, the term of this patent is extended or adjusted under 35 U.S.C. 154(b) by 947 days.

(21) Appl. No.: 17/799,920

(22) PCT Filed: Feb. 17, 2021

(86) PCT No.: PCT/IL2021/050185
§ 371 (c)(1),
(2) Date: Aug. 15, 2022

(87) PCT Pub. No.: WO2021/165960
PCT Pub. Date: Aug. 26, 2021

(65) Prior Publication Data

US 2023/0084299 A1 Mar. 16, 2023

Related U.S. Application Data

(60) Provisional application No. 63/060,165, filed on Aug. 3, 2020, provisional application No. 62/978,324, filed on Feb. 19, 2020.

(51) Int. Cl.

| | |
|---|---|
| ***A61K 31/439*** | (2006.01) |
| ***A61K 31/135*** | (2006.01) |
| ***A61K 31/343*** | (2006.01) |
| ***A61K 31/55*** | (2006.01) |
| ***A61P 25/28*** | (2006.01) |

(52) U.S. Cl.
CPC .......... *A61K 31/439* (2013.01); *A61K 31/135* (2013.01); *A61K 31/343* (2013.01); *A61K 31/55* (2013.01); *A61P 25/28* (2018.01)

(58) Field of Classification Search
CPC .. A61K 31/439; A61K 31/135; A61K 31/343; A61K 31/55; A61P 25/28
See application file for complete search history.

(56) References Cited

U.S. PATENT DOCUMENTS

| | | | |
|---|---|---|---|
| 6,235,771 | B1 | 5/2001 | Shiraishi |
| 6,268,354 | B1 | 7/2001 | Nishimura |
| 6,586,430 | B1 | 7/2003 | Armour |
| 6,627,651 | B1 | 9/2003 | Shiraishi |
| 6,667,314 | B2 | 12/2003 | Perros |
| 6,689,783 | B2 | 2/2004 | Clader |
| 6,936,602 | B1 | 8/2005 | Shiraishi |
| 7,368,460 | B2 | 5/2008 | Perros |
| 7,384,944 | B2 | 6/2008 | Baroudy |
| 7,576,097 | B2 | 8/2009 | Perros |
| 2004/0038982 | A1 | 2/2004 | Bondinell |
| 2008/0021038 | A1 | 1/2008 | Tucker |
| 2014/0057940 | A1 | 2/2014 | Mankowski |

FOREIGN PATENT DOCUMENTS

| | | | |
|---|---|---|---|
| WO | 9825604 | A1 | 6/1998 |
| WO | 9825605 | A1 | 6/1998 |
| WO | 9825617 | A1 | 6/1998 |
| WO | 9827815 | A1 | 7/1998 |
| WO | 9830218 | A1 | 7/1998 |
| WO | 9831364 | A1 | 7/1998 |
| WO | 9901127 | A1 | 1/1999 |
| WO | 9909984 | A1 | 3/1999 |
| WO | 9932100 | A2 | 7/1999 |
| WO | 2012097062 | A1 | 7/2012 |
| WO | 2019135995 | A1 | 7/2019 |

OTHER PUBLICATIONS

MacArthur et al. (Reviews of Anti-Infective Agents, CID 2008:47, 236-241). (Year: 2008).*

Joy, Mary T., et al. "CCR5 is a therapeutic target for recovery after stroke and traumatic brain injury." Cell 176.5 (2019): 1143-1157. (Year: 2019).*

Oglodek, Ewa A., et al. "Comparison of chemokines (CCL-5 and SDF-1), chemokine receptors (CCR-5 and CXCR-4) and IL-6 levels in patients with different severities of depression." Pharmacological Reports 66.5 (2014): 920-926. (Year: 2014).*

(Continued)

*Primary Examiner* — James H Alstrum-Acevedo
*Assistant Examiner* — Justin Christopher Sanchez
(74) *Attorney, Agent, or Firm* — FULLER IP LAW LLC; Rodney J. Fuller

(57) ABSTRACT

The invention relates to the treatment of depressive and anxiety disorders, specifically to improved therapy for patients afflicted with post-stroke depression and/or anxiety, or with major depressive disorder. More specifically, the invention relates to the use of chemokine receptor (CCR5) inhibitors, either alone or in combination with antidepressants such as selective serotonin reuptake inhibitors (SSRIs) and serotonin-norepinephrine reuptake inhibitors (SNRIs), in treating depression and anxiety, as well as certain post-stroke complications that may include cognitive impairment. Compositions and methods according to embodiments of the invention are advantageously useful in the treatment of patients with treatment-resistant depression and other patient populations in which conventional antidepressant therapy is inadequate or insufficient.

17 Claims, 7 Drawing Sheets

(56) References Cited

OTHER PUBLICATIONS

Vojvodic, Jovana, et al. "The impact of immunological factors on depression treatment-relation between antidepressants and immunomodulation agents." Open access Macedonian journal of medical sciences 7.18 (2019): 3064. (Year: 2019).*
Ndhlovu, Lishomwa C., et al. "Treatment intensification with maraviroc (CCR5 antagonist) leads to declines in CD16-expressing monocytes in cART-suppressed chronic HIV-infected subjects and is associated with improvements in neurocognitive test performance: implications for (Year: 2014) HIV-associated neurocognitive disease (HAND)." Journal of neurovirology 20.6 (2014): 571-582. (Year: 2014).*
Carter, Natalie J., and Gillian M. Keating. "Maraviroc." Drugs 67.15 (2007): 2277-2288 (Year: 2007).*
Schöttke, Henning, and Claire-Marie Giabbiconi. "Post-stroke depression and post-stroke anxiety: prevalence and predictors." International psychogeriatrics 27.11 (2015): 1805-1812 (Year: 2015).*
Liu, Wei, et al. "The role of neural plasticity in depression: from hippocampus to prefrontal cortex." Neural plasticity 2017.1 (2017): 6871089. (Year: 2017).*
Joy et al., (2019) CCR5 Is a Therapeutic Target for Recovery after Stroke and Traumatic Brain Injury. Cell 176(5): 1143-1157.e13.
Asano et al., (2014) Preparation and activities of macromolecule conjugates of the CCR5 antagonist Maraviroc. ACS Med Chem Lett 5(2): 133-137.
Banisadr et al., (2002) Neuroanatomical distribution of CXCR4 in adult rat brain and its localization in cholinergic and dopaminergic neurons. Eur J Neurosci 16(9): 1661-1671.
Cho and Miller (2002) Chemokine receptors and neural function. J Neurovirol 8(6): 573-584.
Fazekas et al., (1987) MR signal abnormalities at 1.5 T in Alzheimer's dementia and normal aging. AJR Am J Roentgenol 149(2): 351-356.
Fazekas et al., (1993) Pathologic correlates of incidental MRI white matter signal hyperintensities. Neurology 43(9): 1683-1689.
Greeson et al., (2016) The Selective Serotonin Reuptake Inhibitor Citalopram Decreases Human Immunodeficiency Virus Receptor and Coreceptor Expression in Immune Cells. Biol Psychiatry. Author manuscript; available in PMC Jul. 1, 2017. Published in final edited form as: Biol Psychiatry. Jul. 1, 2016; 80(1): 33-39.
Haroon et al., (2012) Psychoneuroimmunology meets neuropsychopharmacology: translational implications of the mpact of inflammation on behavior. Neuropsychopharmacology 37(1): 137-162.
Joy et al., (2012) CCR5 Is a Therapeutic Target for Recovery after Stroke and Traumatic Brain Injury. Cell 176(5): 1143-1157.e13.
Kok et al., (2012) Efficacy of treatment in older depressed patients: a systematic review and meta-analysis of double-blind randomized controlled trials with antidepressants. J Affect Disord 141(2-3): 103-115.
Larsen et al., (2016) Structure-activity relationship studies of citalopram derivatives: examining substituents conferring selectivity for the allosteric site in the 5-HT transporter. Br J Pharmacol 173(5): 925-936.
Maayan et al., (2000) Evidence for recent selection of the CCR5-delta 32 deletion from differences in its frequency between Ashkenazi and Sephardi Jews. Genes Immun 1(6): 358-361.
Mondal et al., (2019) Low-Dose Maraviroc, an Antiretroviral Drug, Attenuates the Infiltration of T Cells into the Central Nervous System and Protects the Nigrostriatum in Hemiparkinsonian Monkeys. J Immunol 202(12): 3412-3422.
Mukai and Tampi (2009) Treatment of depression in the elderly: a review of the recent literature on the efficacy of single- versus dual-action antidepressants. Clin Ther 31(5): 945-961.
Ndhlovu et al., (2014) Treatment intensification with maraviroc (CCR5 antagonist) leads to declines in CD16-expressing monocytes in cART-suppressed chronic HIV-infected subjects and is associated with improvements in neurocognitive test performance: implications for HIV-associated neurocognitive disease (HAND). J Neurovirol. Author manuscript; available in PMC Dec. 1, 2015. Published in final edited form as: J Neurovirol. Dec. 2014; 20(6): 571-582.
Ogłodek et al., (2014) Comparison of chemokines (CCL-5 and SDF-1), chemokine receptors (CCR-5 and CXCR-4) and IL-6 levels in patients with different severities of depression. Pharmacol Rep 66(5): 920-926.
Pigott et al., (2010) Efficacy and effectiveness of antidepressants: current status of research. Psychother Psychosom 79(5): 267-279.
Raedler (2011) Inflammatory mechanisms in major depressive disorder. Curr Opin Psychiatry 24(6): 519-525.
Samson et al., (1996) Resistance to HIV-1 infection in caucasian individuals bearing mutant alleles of the CCR-5 chemokine receptor gene. Nature 382(6593): 722-725.
Sawchuck C.: "Depression and anxiety: Can I have both?"; retrieved from internet: URL: <https://www.mayoclinic.org/diseases-conditions/depression/expert-answers/depression-and-anxiety/faq-20057989/>, [Retrieved on May 13, 2021] Jun. 2, 2017 (Jun. 2, 2017).
Turner (2013) Publication bias, with a focus on psychiatry: causes and solutions. CNS Drugs 27(6): 457-468.
Van der Meer et al., (2000) Immunohistochemical analysis of CCR2, CCR3, CCR5, and CXCR4 in the human brain: potential mechanisms for HIV dementia. Exp Mol Pathol 69(3): 192-201.
Vojvodic et al., (2019) The Impact of Immunological Factors on Depression Treatment—Relation Between Antidepressants and Immunomodulation Agents. Open Access Maced J Med Sci 7(18):3064-3069.

* cited by examiner

ANTIDEPRESSANT THERAPY

CROSS-REFERENCE TO RELATED APPLICATIONS

This application is the U.S. National Stage of International Patent Application No. PCT/IL2021/050185, filed on Feb. 17, 2021, which claims the benefit of and priority to U.S. Provisional Patent Application Nos. 63/060,165, filed on Aug. 3, 2020, and 62/978,324, filed on Feb. 19, 2020, the contents of each of which are hereby incorporated by reference in their entireties.

FIELD OF THE INVENTION

The invention relates to the treatment of depressive and anxiety disorders, specifically to improved therapeutic modalities for post-stroke depression, post-stroke anxiety, treatment-resistant depression, and depression that does not sufficiently respond to current available treatments, using chemokine receptor 5 (CCR5) modulators.

BACKGROUND OF THE INVENTION

The World Health Organization has projected that major depressive disorder (MDD) will be the second leading cause of disability worldwide by 2030. The lifetime risk of MDD is 7% to 12% for men, and 20% to 25% for women. Depression is associated with decreased quality of life and increased mortality. The prevalence of depression among the elderly in Europe is estimated to be about 10-15%. Although MDD is the most prevalent mental disorder among elderly patients, the condition often remains inadequately treated. Extensive data supports the efficacy of antidepressants in patients with MDD, yet only modest remission rates are usually achieved with first-step antidepressants, and gaps in our knowledge remain as to the choice of second- or third-line treatments if first step antidepressants fail.

About half of patients with depression require a second-line treatment to achieve remission, following inadequate response to the first-line treatment, which is usually a selective serotonin reuptake inhibitor (S SRI).

Current anti-depressants in use are mostly SSRIs, Serotonin-Norepinephrine Reuptake Inhibitors (SNRIs), and the older tricyclic antidepressants (TCAs). All three drug families—SSRIs, SNRIs and TCAs—are known to block reuptake of the neurotransmitter serotonin by the pre-synaptic neuron. While SSRIs are relatively specific in this action, SNRIs block also the noradrenaline transporter, and TCAs block both these transporters aside from blocking histaminic, cholinergic, and alpha1-adrenergic receptor sites in the post synaptic neuron. This lack of selectivity is associated with unwanted side effects such as weight gain, dry mouth, constipation, drowsiness, and dizziness. SSRIs, although more specific in action, are also associated with burdening side effects such as weight gain and sexual dysfunction. In addition, although the inhibition of the transporter is measurable soon after drug treatment, clinically beneficial effects are obtained only after a prolonged period of use, typically several weeks.

The Sequenced Treatment Alternatives to Relieve Depression (STAR*D) trial is the largest prospective, randomized treatment study to date of outpatients with MDD recruited from "real world" psychiatric and primary care settings. The study demonstrated that for at least 70% of patients, appropriate treatment with a SSRI was not adequate to achieve remission. Remission rates of approximately 50% to 55% were reported after two sequential treatment interventions in the STAR*D trial. The probabilities of achieving remission with third- and fourth-step therapy were considerably lower, i.e., ≤25%. STAR* D results showed that antidepressants were not optimal in achieving remission in "real-world patients" suffering from depression, and suggested that a vigorous treatment approach is warranted in many of these patients, specifically those who did not fully respond to 1$^{st}$ line therapies. The treatment provided, consistent with the theoretical principles and clinical beliefs that currently guide the management of treatment-resistant depression, proved to be very partially effective. This admittedly harsh assessment is most evident when using study completion rates as the best 'hard measure of treatment effectiveness and acceptability'. Turner et al. (2013, CNS Drugs 27, 457-468) demonstrates how publication bias inflates the perceived efficacy of antidepressants, thereby promoting the widespread acceptance of this treatment. Despite the pervasive belief regarding the effectiveness of antidepressants and cognitive behavioral therapy (CBT) among physicians and society at large, STAR*D showed that antidepressants and CBT fail to result in sustained positive effects for the majority of people who receive them (Pigott et al., 2010, Psychother Psychosom 79, 267-279). Recent meta-analysis study of 51 double-blind randomized controlled trials suggests that SSRIs and SNRIs do not exhibit differential efficacy compared to the older TCAs in elderly patients (Kok et al., 2012, J Affect Disord 141, 103-115). Furthermore, SSRIs also appeared to be less effective in patients with severe depression (Mukai et al., 2009, Clin Ther 31, 945-961).

Thus, the existing anti-depressants present limited efficacy in general and in particular in the elderly. Treatment-refractory or treatment-resistant depression (TRD), defined as major depressive disorder that does not respond to at least two adequate courses of antidepressants, remains a major challenge to both clinicians and researchers. Another clinical problem is posed by a relatively large subgroup of patients who do respond to anti-depressant therapy, yet their response is sub-optimal and they fail to achieve remission. This very wide sub-group of patients raises serious clinical questions as to the optimal therapeutic approach (e.g. whether the clinician should change the drug used, add on another drug, or use a different treatment modality).

Post-stroke depression (PSD) is a form of depression that appears in relation to ischemic or hemorrhagic intracranial events, and is the most frequent neuropsychiatric sequela of stroke, with a prevalence rate of 18% to 61% (a 3-fold increase when compared to the general population). PSD is associated with increased mortality, higher disability, lower quality of life and a greater risk of cognitive decline when compared to stroke survivors without depression.

Currently there are no "gold standard" therapies for PSD or post stroke anxiety symptoms. Current available therapeutic options do not differ from those recommended for MDD patients. However, stroke survivors are especially susceptible to side effects of SSRIs, such as hyponatremia, that can limit their use in these patients.

Accumulating evidence suggests that inflammatory processes, neural-immune interactions, and neurodegenerative processes are involved in PSD. Related theories focus on synaptic plasticity as an important means of recovery from PSD, after converged molecular and cellular mechanisms including inflammation cause atrophy of neurons, loss of glutamatergic synaptic connections and dysfunction of the circuitry that is essential for mood regulation and cognitive function. Indeed, PSD can be perceived as a psychoneuroimmunological disorder in which inflammatory mechanisms involving cytokines and chemokines play a role (Raedler T J, et al., 2011, Curr Opin Psychiatry 24, 519-525; Oglodek, E A, 2014, Pharm Rep 66(5), 920-926). Both acute stroke patients and depressed patients consistently show higher levels of pro-inflammatory cytokines, acute phase proteins, chemokines and cellular adhesion molecules.

Chemokines are a large family of structurally related small proteins that act as inflammatory factors and share the ability to induce chemotaxis, tissue extravasation and to modulate leukocyte functions. In the central nervous system (CNS), chemokine receptors are constitutively expressed on neural cells (van de Meer et al., 2000, Exp Mol Pathol 69, 192-201; Banisadr et al., 2002, J Neurosci 16, 1661-1671) and are suggested to be involved in cellular communication. Chemokines were suggested to exhibit various roles in regulating neurogenesis, neuroinflammation, neuromodulation and neuroendocrine functions. Chemokine receptor activation in neurons induces calcium transients and modulates ion channel activity/excitability (Cho et al., 2002, J Neurovirol 8, 573-584). Oglodek et al. (Pharm Rep 66(5), 920-926, 2014) evaluated the levels of chemokines (CCL-5 and SDF-1), chemokine receptors (CCR-5 and CXCR-4) and IL-6 in patients with different severities of depression as compared to their levels in control groups.

C—C chemokine receptor type 5, also known as CCR5 or CD195, belongs to the beta chemokine receptors family of integral membrane proteins. CCR5's cognate ligands include CCL3, CCL4 (also known as MIP 1α and 1β, respectively), CCL3L1, and CCL5 (a chemotactic cytokine protein also known as RANTES). Many forms of the human immunodeficiency virus (HIV), commonly use the chemokine receptor CCR5 as a co-receptor to enter target immune cells. Serotonin and the SSRI citalopram were suggested to affect HIV-1 replication and modulate CCR5 expression on peripheral blood mononuclear cells and macrophages (Greeson et al., 2016, Biological Psychiatry 80, 33-39).

CCR5 is known to be involved in immune processes and neuroplasticity and is highly expressed in T cells and macrophages, as well as in microglia, astrocytes and neurons in multiple brain regions. CCR5 is a pro-inflammatory receptor and inhibition of its signaling has been shown to enhance plasticity processes in hippocampal and cortical circuits. Other reports showed that CCR5 blockade attenuated activation of glial cells, maintained the integrity of endothelial monolayer, reduced the infiltration of T cells, and attenuated neuroinflammation (Mondal, S., et al., 2019, J Immunol).

A human CCR5 gene that involves a 32 bp deletion (CCR5-Δ32 mutation) and resultant loss of function in the receptor, rendering resistance to HIV infection, has been well-characterized (Samson et al., 1996, Nature 382, 722-725; Maayan et al., 2000 Genes Immun 1, 358-361). The global, ethnic, and regional distribution of the CCR5-Δ32 allele varies significantly among different populations. The CCR5-Δ32 allele is relatively common in Caucasians whose allelic frequency is ~10%, and homozygosity is found in 1% of Caucasian blood donors, with the highest frequency reported in Ashkenazi Jews.

Haroon et al. (Neuropsychopharmacology, 37(1), 137-162, 2012) refer to the potential contribution of chronic inflammation to the development of neuropsychiatric disorders such as depression, and suggest an increasing need to test neuropharmacological strategies that target the immune system to treat such disorders. Haroon et al. report that the CCR5 inhibitor maraviroc is used for treating HIV and the CXCR4 inhibitor Plerixafor is used for stem cell mobilization; however, the results in clinical trials for inflammatory disorders using chemokine receptor modulators are disclosed to be rather disappointing, despite promising results in animal models.

US 2014/057940 relates to methods for treating or preventing cardiac and neurological disorders using chemokine receptor antagonists. The '940 publication names depression among extensive lists of disorders, and CCR5 among various chemokine receptors. The publication further discloses that maraviroc inhibited simian immunodeficiency virus (SIV)-mediated CNS disease in rhesus macaques, as manifested by SIV RNA levels in CSF and brain, macrophage activation represented by CD68 immunostaining and axonal APP immunostaining.

US 2008/021038 discloses piperidine/8-azabicyclo [3.2.1.] octan derivatives that are CCR5 modulators, and therapeutic use thereof. US '038 discloses that the compounds may be administered in combination with another therapeutic agent or agents. Among the various drugs and drug families mentioned in US '038 are CNS agents including an antidepressant such as sertraline.

Various other small molecule CCR5 inhibitors and antagonists are disclosed, for example, in U.S. Pat. No. 7,384,944 (piperazine derivatives), U.S. Pat. No. 6,689,783 (aryl oxime-piperazines), WO99/32100 (anilide derivatives); U.S. Pat. Nos. 6,268,354, 6,627,651, 6,235,771 (anilide derivatives), U.S. Pat. No. 6,936,602 (benzazepine derivatives); WO 98/25604, WO 98/25605, WO 98/25617, WO 98/27815, WO 98/30218, WO 98/31364, WO 99/01127 (substituted benzanilides), WO99/09984 (pyrrolidine and piperidine compounds); and US 2004/0038982 (substituted heterocyclic compounds).

Maraviroc (Selzentry® or Celsentri®) is a CCR5 co-receptor antagonist, indicated for combination antiretroviral treatment of adults infected with only CCR5-tropic HIV-1. Maraviroc is an entry inhibitor, specifically, a negative allosteric modulator of the CCR5 receptor, which binds to CCR5, thereby blocking the HIV protein gp120 from associating with the receptor.

The molecular formula maraviroc is $C_{29}H_{41}F_2N_5O$ and the structural formula is:

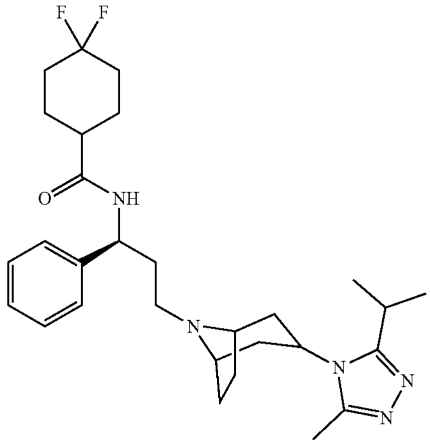 [SMILES: Cc1nnc(C(C)C)n1C1CC2CCC(C1)N2CC[C@H](NC(=O)C1CCC(F)(F)CC1)c1ccccc1]

The most common adverse events in treatment-experienced subjects, which occurred at a higher frequency compared with placebo, are upper respiratory tract infections, cough, pyrexia, rash, and dizziness. Depressive disorders and anxiety symptoms have also been reported as potential treatment-emergent adverse events, based on the pooled data from two trials in subjects with CCR5-tropic HIV-1.

Maraviroc (Selzentry®) and/or related compounds are referred to in U.S. Pat. Nos. 6,586,430, 6,667,314, 7,368,460 and 7,576,097.

The effects of various chemokine antagonists, including maraviroc and other CCR5 inhibitors, has been tested in a variety of systems and models, including in neurons and the central nervous system. For example, US 2014/0057940 relates to methods for treating or preventing cardiac and neurological disorders using chemokine receptor antagonists. WO 2019/135995 relates to compositions and methods for treating a neurological disorder in a subject, comprising administering to the subject a therapeutically effective amount of a CCR5 antagonist, e.g. maraviroc. The neurological disorder is in particular Alzheimer's disease, Parkinson's disease, dementia with Lewy bodies or multiple system atrophy. Mondal et al (J Immunol Jun. 15, 2019, 202 (12) 3412-3422) shows that maraviroc attenuates the infiltration of T cells into the central nervous system and protects the nigrostriatum in hemiparkinsonian monkeys.

The present inventor and co-workers have recently reported that post-stroke neuronal knockdown of CCR5 in pre-motor cortex leads to early recovery of motor control (Joy, M. T., et al., Cell 176: 1143-1157, 2019). It was shown that in a clinical cohort of stroke patients, carriers of the CCR5-Δ32 mutation exhibited greater recovery of neurological impairments and cognitive function (Joy, M. T., et al., ibid).

There remains an unmet medical need for improved treatments for depressive and anxiety disorders, in particular for post-stroke depression and anxiety as well as for treatment-resistant depression and depression that does not sufficiently respond to current available treatments.

SUMMARY OF THE INVENTION

The invention provides treatment of depressive and anxiety disorders, specifically for patients afflicted with, or at risk for developing, post-stroke depression (PSD) and/or post-stroke anxiety (PSA). The invention further provides treatment for treatment-resistant depression (TRD), for major depressive disorder (MDD) that responds sub-optimally to currently available treatments, and for MDD. More specifically, the invention provides use of chemokine receptor 5 (CCR5) inhibitors, either alone or in combination with selective serotonin reuptake inhibitors (SSRIs) or Serotonin-Norepinephrine Reuptake Inhibitors (SNRIs), in compositions and methods for treating post-stroke depression and anxiety. Compositions and methods according to embodiments of the invention are advantageously useful in the treatment of patients with treatment-resistant depression and other patient populations in which conventional antidepressant therapy is inadequate, insufficient, or associated with adverse effects. In addition, compositions and methods of the invention can be effective in treating or inhibiting depressive and anxiety symptoms in subjects following stroke or transient ischemic attack.

The invention is based, in part, on the surprising discovery that a very low frequency of depression exists among carriers of the CCR5-Δ32 (rs333) mutation, characterized by loss of function of CCR5, in a group of post stroke patients. In a study conducted in a prospective stroke cohort, carriers of the CCR5-Δ32 allele were unexpectedly more protected than non-carriers from the development of depressive or anxiety symptoms for a long period of time, i.e., for up to two years after the stroke. The results were even more prominent in women. The post-stroke cohort study further showed that carriers of the CCR5-Δ32 allele who had no detectable white matter lesions (WMLs) or had mild WMLs upon hospital admission were highly protected from developing post-stroke depressive and post-stroke anxiety symptoms. The post-stroke cohort study showed that even carriers of the CCR5-Δ32 allele who had severe WMLs manifested less depressive and anxiety symptoms compared to non-carriers of the deletion.

The invention is further based, in part, on unexpectedly advantageous effects of the CCR5 inhibitor maraviroc when used for the first time as an antidepressant in clinical settings. Specifically, in a clinical study conducted to evaluate the safety, tolerability and efficacy of maraviroc in human patients suffering from post-stroke depression (PSD), maraviroc was found to be effective in the inhibition and reversal of depressive and anxiety symptoms in all patients, and was well-tolerated without safety concerns. Surprisingly, an extraordinarily short time to response of 1-2 weeks was reported in all treated subjects, as opposed to a typical response time of 4 weeks and above for most SSRIs and SNRIs. Further, all patients exhibited a marked reduction in depression scores, from a score at admission of >34 at the Montgomery-Asberg Depression Rating Scale (MADRS) (corresponding to severe major depressive disorder, MDD) to a MADRS score of <20 (mild depression), or even <7 (remission, normal/symptom-absent), within a short period of time of several weeks. The effects were observed when maraviroc was used as monotherapy, as well as when administered in combination with other drugs (such as SSRIs) to which the subjects had previously failed to respond.

Accordingly, maraviroc was unexpectedly found to be particularly effective in the treatment of MDD, and in particular post-stroke depression and anxiety in human subjects, including in TRD patients.

In accordance with embodiments of the invention, CCR5 modulators such as maraviroc, which mimic the effects of the CCR5-Δ32 mutation in humans, are disclosed herein as unexpectedly effective therapies for depressive disorders. Thus, rather than being associated with enhanced risk for developing depression and anxiety, maraviroc can be used according to embodiments of the invention in treating and preventing depressive and anxiety symptoms. According to some embodiments, CCR5 inhibitors such as maraviroc, used either alone or in combination with one or more SSRIs or SNRIs, may provide improved efficacy, enhanced safety, and/or shorten the treatment lag (shorten the time required to achieve significant symptom alleviation).

Accordingly, embodiments of the invention relate to methods for the treatment of a depressive and/or anxiety disorder in a subject in need thereof. In another embodiment, the subject is human. In another embodiment, the subject is female. In another embodiment, the subject is over 50 years of age. In another embodiment, the subject is elderly (over 65 years of age). In a particular embodiment, the subject is a human female over 50 years of age, or over 65 years of age. In another embodiment, the subject is diagnosed with a recent stroke.

In another embodiment, the method is used for treating, preventing or inhibiting depressive and/or anxiety symptoms. In another embodiment, the method is used for preventing or inhibiting depressive and anxiety symptoms. In another embodiment, the subject is at risk for developing a depressive and/or anxiety disorder, e.g. MDD or TRD. In another embodiment, the method is used for preventing or inhibiting post-stroke depression.

In another embodiment, the method comprises administering to the subject an effective amount of a CCR5 inhibitor or antagonist. In another embodiment, the inhibitor is maraviroc (or a derivative thereof). In another embodiment, the CCR5 inhibitor used in compositions, methods, kits and pharmaceutical packs of the invention may be e.g., a compound antagonizing the binding of CCR5 to its ligand (e.g. small molecule antagonist), a neutralizing antibody to CCR5, an isolated peptide derived from the sequences of CCR5 or analogs thereof capable of inhibiting CCR5, or a CCR5-downregulating nucleic acid (e.g. an antisense nucleic acid, a silencing RNA molecule, an antagonist microRNA, and an enzymatic RNA molecule). Each possibility represents a separate embodiment of the invention. In a particular embodiment, the small molecule antagonist is maraviroc.

In another embodiment, there is provided a method for treating or inhibiting the symptoms of a depressive and/or anxiety disorder in a subject in need thereof, comprising administering to the subject an effective amount of maraviroc or a derivative thereof.

In another embodiment, the inhibitor (e.g., maraviroc) is administered in combination with at least one anti-depressant in patients who do not respond sufficiently to an anti-depressant. In some embodiments, the antidepressant is selected from the group consisting of SSRIs, SSNRIs, and TCAs. In another embodiment, the antidepressant is a S SRI. In another embodiment, the CCR5 inhibitor is administered as a sole active ingredient.

In another aspect, the invention provides a method for treating or inhibiting the symptoms of a depressive and/or anxiety disorder selected from the group consisting n need thereof, comprising administering to the subject a pharmaceutical composition comprising a therapeutically effective amount of maraviroc or a derivative thereof. In another aspect, the invention provides a method for treating or inhibiting the symptoms of a depressive and/or anxiety disorder selected from the group consisting of PSD, PSA, TRD, MDD that does not adequately respond to an antidepressant, and MDD, in a subject in need thereof, comprising administering to the subject a pharmaceutical composition comprising a therapeutically effective amount of maraviroc or a derivative thereof. Each possibility represents a separate embodiment of the invention.

In another embodiment, the therapeutically effective amount of maraviroc is 100 mg per day to 300 mg per day. In a further embodiment, the therapeutically effective amount is 125 mg per day to 250 mg per day, preferably administered once daily. In still further embodiment, said therapeutically effective amount is about 150 mg per day administered orally once daily. Each possibility represents a separate embodiment of the invention.

In another embodiment, the subject manifests both depressive and anxiety symptoms. In a further embodiment, the subject is at high risk of suicidal ideation and/or suicidal behavior evaluated by the Columbia Suicide Severity Rating Scale (C-SSRS). In a further embodiment, the subject is at high risk of suicidal behavior evaluated by C-SSRS. In another embodiment, the subject is a human female. In another embodiment, said subject is over 50 years of age or over 65 years of age. In another embodiment, the subject is diagnosed as being afflicted with post-stroke depression and/or post-stroke anxiety. In another embodiment, the subject has been diagnosed with cerebral infarction or transient ischemic attack two weeks to two years prior to administration of the maraviroc or derivative thereof, e.g. 1-24 months, 4-36 months, 4-24 months, 4-18 months 6-12 months or up to 8-12 months, or any integer in between, prior to administration of the maraviroc or derivative thereof. In a particular embodiment, the subject has been diagnosed with cerebral infarction or transient ischemic attack 4-24 months prior to administration of the maraviroc or derivative thereof.

In another embodiment, the subject is diagnosed with post-stroke depression/depressive symptoms and/or post-stroke anxiety/anxiety symptoms one month to two years after stroke occurrence, or 1-24 months after stroke occurrence, or 4-18 months after stroke occurrence, 6-12 months after stroke occurrence, or up to 8-12 months after stroke occurrence. In another embodiment, the subject is further diagnosed with post-stroke cognitive impairment (PSCI). In another embodiment, said subject is diagnosed with WMLs prior to treatment. In another embodiment, said subject is diagnosed with lack of WMLs prior to treatment. In another embodiment, the subject is diagnosed with mild to moderate WML load (evaluated by grading scale 1-2) on the Fazekas score (Fazekas F, et al., 1987, AJR Am J Roentgenol; 149(2):351-6, Fazekas F, et al., 1993, Neurology 43(9), 1683-9). In another embodiment, said subject is diagnosed with severe WML load (evaluated by grading scale 3) on the Fazekas score (Fazekas F, et al., ibid). Each possibility represents a separate embodiment of the invention.

In a further embodiment, administering the pharmaceutical composition is performed once a day for at least one month, for at least two months, for at least three months, for 1-3 months, for one year, or so long as the symptoms of the depressive and/or anxiety disorder are ameliorated, weakened or disappear. Each possibility represents a separate embodiment of the invention. In a particular embodiment administering the pharmaceutical composition is performed once a day for 1-3 months, or so long as the symptoms of a depressive and/or anxiety disorder are ameliorated or disappear.

In another embodiment, the method comprises administering to said subject maraviroc in concurrent or sequential combination with at least one antidepressant. In a particular embodiment, the antidepressant is a SSRI or a SNRI. In another embodiment said subject is resistant to treatment with at least one of citalopram, escitalopram, sertraline, mirtazapine, and combinations thereof. In another embodiment the method comprises administering to said subject maraviroc in combination with citalopram, escitalopram, sertraline, mirtazapine, or combinations thereof. In another embodiment, said method comprises administering to said subject maraviroc as a sole active ingredient.

In another aspect, there is provided a method for treating TRD in a human subject in need thereof, comprising administering to the subject a pharmaceutical composition comprising a therapeutically effective amount of a CCR5 inhibitor or antagonist. In another embodiment, the CCR5 inhibitor is selected from the group consisting of: a compound antagonizing the binding of CCR5 to its ligand, a neutralizing antibody to CCR5, an isolated peptide derived from the sequences of CCR5 or analogs thereof capable of inhibiting CCR5, or a CCR5-downregulating nucleic acid (e.g., an antisense nucleic acid, a silencing RNA molecule, an antagonist microRNA, and an enzymatic RNA molecule). In a particular embodiment, the CCR5 inhibitor is maraviroc or a derivative thereof. In another embodiment, the method comprises administering to said subject maraviroc in concurrent or sequential combination with at least one antidepressant (e.g., SSRI or SNRI). In a particular embodiment, the antidepressant is a SSRI. In another embodiment said subject is resistant to treatment with at least one of citalopram, escitalopram, sertraline, mirtazapine, and combinations thereof. In another embodiment the method comprises administering to said subject maraviroc in combination with citalopram, escitalopram, sertraline, mirtazapine, or combinations thereof. In another embodiment, the method comprises administering to said subject maraviroc as a sole active ingredient. In another embodiment, the therapeutically effective amount of maraviroc is 100 mg per day to 300 mg per day, or 125 mg per day to 250 mg per day, or 150 mg per day, preferably administered once daily. In a further embodiment, the subject is at high risk of suicidal ideation and/or suicidal behavior evaluated by the Columbia Suicide Severity Rating Scale (C-SSRS). In a particular embodiment said subject is at high risk of suicidal behavior evaluated by C-SSRS. In other embodiments, the method comprises administering maraviroc in a treatment regimen as disclosed herein. Each possibility represents a separate embodiment of the invention.

In another aspect, the invention provides a method for enhancing the efficacy of an antidepressant treatment, comprising administering the treatment in concurrent or sequential combination with a CCR5 inhibitor or antagonist, thereby enhancing the efficacy of the antidepressant treatment. In another embodiment the CCR5 inhibitor is maraviroc. In another embodiment the antidepressant treatment is a SSRI. In another embodiment the CCR5 inhibitor is maraviroc and the antidepressant treatment is a SSRI. In another embodiment the SSRI is selected from the group consisting of citalopram, escitalopram, sertraline, and combinations thereof. In another embodiment maraviroc is administered in concurrent or sequential combination with a plurality of antidepressants (e.g. SSRIs or other antidepressants as disclosed herein). In another embodiment, enhancing the efficacy of the antidepressant treatment comprises providing a more rapid onset of therapeutic efficacy. In another embodiment, the subject is at high risk of suicidal ideation and/or suicidal behavior evaluated by C-SSRS. In a particular embodiment said subject is at high risk of suicidal behavior evaluated by C-SSRS. In another embodiment enhancing the efficacy of the antidepressant comprises inducing remission in said subject. In another embodiment the subject belongs to a patient group as disclosed herein. In another embodiment, the maraviroc is administered at a therapeutically effective amount as disclosed herein. In another embodiment, the maraviroc is administered at a treatment regimen as disclosed herein.

In another aspect, the present invention provides a method of treating post-stroke cognitive impairment (PSCI) in a subject diagnosed with established PSCI, comprising administering to the subject maraviroc in a therapeutically effective amount. In one embodiment, the method comprises administering to the subject maraviroc in a therapeutically effective amount of 100 mg per day to 600 mg per day. In another embodiment the method comprises administering to the subject maraviroc in a therapeutically effective amount of 150 mg per day to 600 mg per day. In another embodiment the method comprises administering to the subject maraviroc in a therapeutically effective amount of 100 mg per day to 300 mg per day. In another embodiment, said therapeutically effective amount is 125 mg per day to 250 mg per day, preferably administered once daily. In a further embodiment, said therapeutically effective amount is about 150 mg per day administered orally once daily. In another embodiment, said therapeutically effective amount is about 300 mg per day administered orally twice daily. In another embodiment, said therapeutically effective amount is about 600 mg per day administered orally once daily. In another embodiment said therapeutically effective amount is about 150 mg per day or about 600 mg per day. In other embodiments, the method comprises administering maraviroc in a treatment regimen as disclosed herein, wherein each possibility represents a separate embodiment of the invention. In another embodiment, treating comprises improving the cognitive score of the subject compared to the score determined prior to treatment, preferably improving in 2 points the cognitive score of said subject compared to the score determined prior to treatment. In a further embodiment, the score is determined based on the Montreal Cognitive Assessment (MoCA), or on a similar score.

In still further embodiment, treating comprises eliminating or reducing the severity of a symptom or clinical sign associated with PSCI compared to its level as determined prior to treatment. In another embodiment, said subject is diagnosed with WMLs prior to treatment. In another embodiment, the subject is diagnosed with mild to moderate WML load evaluated by the Fazekas score (grading scale 1-2). In a further embodiment, said subject is diagnosed with severe WML load evaluated by the Fazekas score (grading scale 3). In another embodiment, said subject has been diagnosed with cerebral infarction or transient ischemic attack (stroke) two weeks to two years prior to administration of the maraviroc (or derivative thereof). In another embodiment, said subject has been diagnosed with cerebral infarction or transient ischemic attack 4-24 months prior to administration of the maraviroc. In another embodiment, said subject has been diagnosed with cerebral infarction or transient ischemic attack 4-36 months prior to administration of the maraviroc. In another embodiment, said subject has been diagnosed with cerebral infarction or transient ischemic attack up to 8-12 months prior to administration of the maraviroc. In another embodiment, the subject is further diagnosed with depression and/or anxiety symptoms within one month to two years after stroke occurrence. In another embodiment, the subject is further diagnosed with depression and/or anxiety symptoms within 3-24 months after stroke occurrence. In another embodiment, the subject is further diagnosed with depression and/or anxiety symptoms within 8-12 months after stroke occurrence. In another embodiment said subject is diagnosed with recent (1-24 months) subcortical stroke and experiences mild PSCI and has evidence of WMLs and small vessel disease (SVD) on neuroimaging. In another embodiment, the subject is as disclosed and exemplified herein. Each possibility represents a separate embodiment of the invention.

In another aspect, there is provided a pharmaceutical composition comprising i) maraviroc (or a derivative thereof), ii) a S SRI, and optionally iii) pharmaceutically acceptable carriers, excipients or diluents, the maraviroc and SSRI provided at amounts effective to treat or prevent depressive and anxiety symptoms in a subject in need thereof. In one embodiment the SSRI is citalopram, or a derivative (or enantiomer) thereof. In another embodiment, the SSRI is selected from the group consisting of citalopram, escitalopram, sertraline, and combinations thereof. In another embodiment said composition consists of maraviroc and an SSRI selected from the group consisting of citalopram, escitalopram, sertraline, and combinations thereof, as the active ingredients. In another embodiment said composition consists of maraviroc and citalopram as the active ingredients. In another embodiment the composition is formulated for oral administration in unit dosage form. In another embodiment, said composition is used in the preparation of a medicament for treating or inhibiting the symptoms of a depressive and/or anxiety disorder in a subject in need thereof. In another embodiment, said composition is for use in treating or inhibiting the symptoms of a depressive and/or anxiety disorder in a subject in need thereof. In another embodiment, said composition is for use in a method as disclosed herein, wherein each possibility represents a separate embodiment of the invention. In another embodiment said composition comprises a therapeutically effective amount of maraviroc as disclosed herein.

In another aspect, the invention relates to kits and pharmaceutical packs, useful for the treatment and prevention of depressive and/or anxiety disorders. In another embodiment, there is provided a pharmaceutical pack, comprising: i) a first pharmaceutical composition comprising maraviroc (or a derivative thereof), ii) a second pharmaceutical composition comprising at least one S SRI, the maraviroc and SSRI provided at amounts effective to treat or prevent depressive and/or anxiety symptoms in a subject in need thereof. In another embodiment, the SSRI is citalopram (or a derivative or enantiomer thereof). In another embodiment the at least one SSRI is selected from the group consisting of citalopram, escitalopram, and sertraline. In another embodiment, said pharmaceutical pack consists of maraviroc and at least one SSRI selected from the group consisting of citalopram, escitalopram, and sertraline as the active ingredients. In another embodiment, said pharmaceutical pack consists of maraviroc and citalopram as the active ingredients. In another embodiment the pack further comprises instructions for administering the first and second pharmaceutical compositions in concurrent or sequential combination to a subject in need thereof, such as a subject in need of treatment of a depressive and/or anxiety disorder (e.g. TRD), as disclosed herein. In another embodiment said pharmaceutical pack comprises a therapeutically effective amount of maraviroc as disclosed herein.

Other objects, features and advantages of the present invention will become clear from the following description and drawings.

BRIEF DESCRIPTION OF THE DRAWINGS

FIG. 1A depicts general linear model (GLM) analysis of repeated measures of depression scores (GDS) in CCR5-Δ32 carriers vs. non-carriers at admission, 6, 12, and 24 months after stroke ($p=0.04$). FIG. 1B depicts depression scores one year after stroke in CCR5-Δ32 carriers vs. non-carriers categorized by groups of white matter lesions (WMLs). FIG. 1C depicts anxiety scores during hospitalization after stroke in CCR5-Δ32 carriers vs. non-carriers categorized by groups of WMLs. FIG. 1D depicts general linear model (GLM) analysis of repeated measures of anxiety scores/post-traumatic symptoms in CCR5-Δ32 carriers vs. non-carriers at 6 and 12 months after stroke. FIG. 1E depicts anxiety scores/post-traumatic stress symptoms one year after stroke in CCR5-Δ32 carriers vs. non-carriers categorized by groups of WMLs. $p<0.001$, #$p=0.052$, for differences between 5-HTTLPR S & CCR5 w.t. to 5-HTTLPR L & CCR5-Δ32. FIG. 1F depicts comparison of the effects of CCR5-Δ32 on anxiety scores/post-traumatic stress symptoms with another genetic variant: Brain-derived neurotrophic factor BDNF Met66 allele and the serotonin-transporter-linked polymorphic region (5-HTTLPR) allele, which has been implicated in the pathophysiology of MDD and anxiety risk. FIG. 1G depicts comparison of the effects of CCR5-Δ32 on anxiety scores/post-traumatic stress symptoms with another genetic variant: the serotonin-transporter-linked polymorphic region (5-HTTLPR) allele, which has been implicated in the pathophysiology of MDD and anxiety risk. FIG. 1**H depicts GLM analysis of repeated measures of longitudinal depression scores at admission, 6, 12, and 24 months after stroke, comparing the four allelic groups of CCR5 and 5-HTTLPR.

DETAILED DESCRIPTION OF THE INVENTION

Figure 1A:
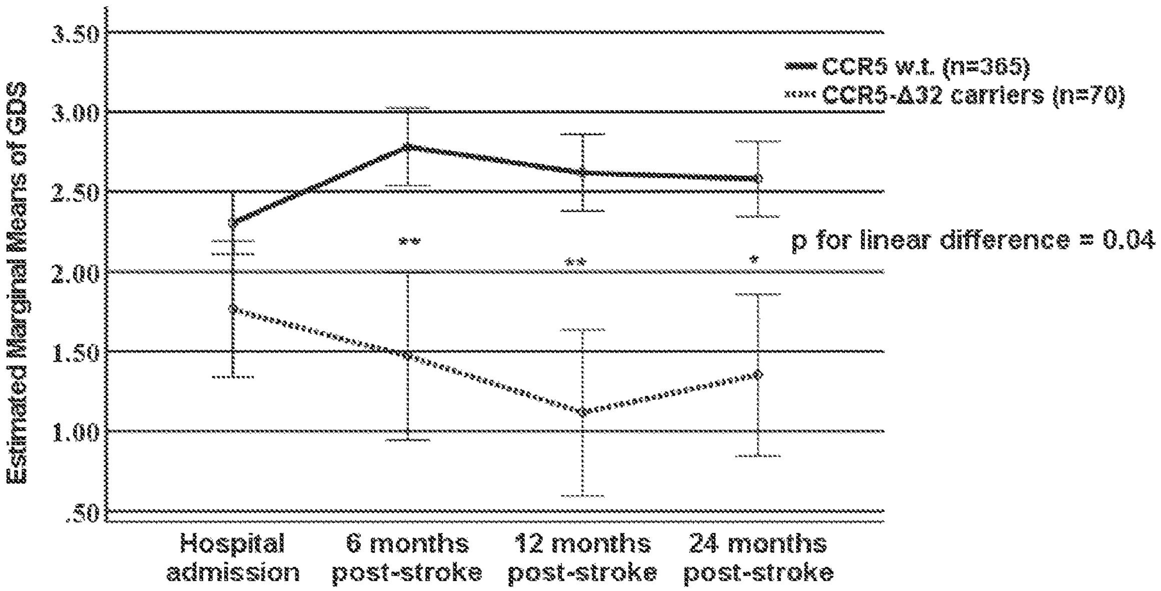
FIGS. 1A-1H depict the involvement of the CCR5-Δ32 mutation on depressive and anxiety symptoms in post-stroke patients.

The invention provides treatment of depressive and anxiety disorders, specifically to improved therapy for patients afflicted with, or at risk for developing, major depressive disorder and/or anxiety. More specifically, the invention provides use of chemokine receptor 5 (CCR5) inhibitors, either alone or in combination with selective serotonin reuptake inhibitors (SSRI), in compositions and methods for treating depression and anxiety. Compositions and methods according to embodiments of the invention are advantageously useful in the treatment of patient populations including, but not limited to, patients with treatment-resistant depression or elderly subjects, in which conventional antidepressant therapy is inadequate, insufficient or involves unwanted adverse events. In addition, compositions and methods of the invention are surprisingly effective in treating or preventing the appearance of depressive and anxiety symptoms in subjects following stroke or transient ischemic attack.

Accordingly, embodiments of the invention relate to methods for the treatment of a depressive and/or anxiety disorder selected from the group consisting of post-stroke depression, post-stroke anxiety, treatment-resistant depression (TRD), major depressive disorder (MDD) that does not adequately respond to an antidepressant, and MDD, in a subject in need thereof. In another embodiment the subject manifests depressive and anxiety symptoms. In another embodiment the subject has been diagnosed with a depressive and/or anxiety disorder, e.g. MDD or TRD.

In one aspect, there is provided a method for treating or inhibiting the symptoms of a depressive and/or anxiety disorder selected from the group consisting of PSD, PSA, TRD, and MDD, in a subject in need thereof, comprising administering to the subject a pharmaceutical composition comprising a therapeutically effective amount of maraviroc or a derivative thereof.

In another aspect, the invention relates to a therapeutically effective amount of maraviroc or a derivative thereof for use in treating or inhibiting the symptoms of a depressive and/or anxiety disorder selected from the group consisting of PSD, PSA, TRD, and MDD, in a subject in need thereof.

In another aspect the invention relates to a method for treating TRD in a human subject in need thereof, comprising administering to the subject a pharmaceutical composition comprising a therapeutically effective amount of a CCR5 inhibitor or antagonist (e.g. maraviroc).

In another aspect the invention relates to a therapeutically effective amount of a CCR5 inhibitor or antagonist (e.g. maraviroc) for use in treating TRD in a human subject in need thereof.

In another aspect, the invention relates to a method for enhancing the efficacy of an antidepressant treatment, comprising administering the treatment in concurrent or sequential combination with a CCR5 inhibitor or antagonist (e.g. maraviroc), thereby enhancing the efficacy of the antidepressant treatment.

In another aspect, the invention relates to a CCR5 inhibitor or antagonist (e.g. maraviroc) for use in enhancing the efficacy of an antidepressant treatment. In another embodiment the use comprises administering the treatment in concurrent or sequential combination with a CCR5 inhibitor or antagonist (e.g. maraviroc), thereby enhancing the efficacy of the antidepressant treatment.

In another aspect there is provided a pharmaceutical composition comprising i) maraviroc, ii) a SSRI, and optionally iii) pharmaceutically acceptable carriers, excipients or diluents, the maraviroc and SSRI provided at amounts effective to treat or prevent the appearance of depressive and anxiety symptoms in a subject in need thereof.

In another aspect the invention provides a pharmaceutical pack, comprising: i) a first pharmaceutical composition comprising maraviroc, ii) a second pharmaceutical composition comprising at least one SSRI, the Maraviroc and SSRI provided at amounts effective to treat or prevent the appearance of depressive and anxiety symptoms in a subject in need thereof.

In another aspect, there is provided method of treating post-stroke cognitive impairment (PSCI) in a subject diagnosed with established PSCI, comprising administering to the subject Maraviroc in a therapeutically effective amount of 100 mg per day to 600 mg per day.

In another aspect, the invention relates to maraviroc for use in treating PSCI in a subject diagnosed with established PSCI. In another embodiment the use comprises administering to the subject maraviroc in a therapeutically effective amount of 100 mg per day to 600 mg per day.

Subjects and Conditions

The compositions, methods and pharmaceutical packs of the invention may be used in various embodiments in the treatment of subjects suffering from symptoms and manifestations of depression and/or anxiety. In some embodiments, the subject to be treated is afflicted with a depressive and/or anxiety disorder, e.g. post-stroke depression (PSD), post-stroke anxiety (PSA), treatment resistant depression (TRD), major depressive disorder (MDD), and combinations thereof, wherein each possibility represents a separate embodiment of the invention. In another embodiment the subject to be treated is afflicted with TRD. In another embodiment the subject to be treated is under treatment regimen with an antidepressant drug or treatment (which may further include drugs and treatments used for managing anxiety symptoms or disorders). According to additional or alternative embodiments, the subject to be treated is diagnosed with established post-stroke cognitive impairment (PSCI). Typically, the subject to be treated by the compositions, methods and pharmaceutical packs of the invention is a human subject.

It is to be appreciated that the methods of the present invention are particularly useful for treating treatment-refractory or treatment-resistant depression (TRD), defined as MDD that does not respond to at least two courses of antidepressants. However, the methods of the present invention are also advantageously useful for treating MDD or symptoms of MDD which have not been sufficiently ameliorated or treated with one course of an antidepressant, we well as in other patient groups in which conventional antidepressant therapy is inadequate or insufficient, as disclosed herein. In another embodiment, the subject is over 50 years of age. In another embodiment the subject is elderly (over 65 years of age). In another embodiment the subject is female. In another embodiment the subject is male.

For example, TRD in patients who received adequate treatment could be defined based on failure to achieve a significant reduction in depressive scores following two distinct anti-depressant pharmacological treatments (also referred to herein as antidepressant drugs or antidepressants) of adequate duration and dose, during the same depressive episode. For example, failure to achieve a reduction of at least 25% in the patient's MADRS score, after two adequate courses of treatment (e.g. by SSRIs and/or SNRIs, typically 4 to 6 weeks once the targeted dose is obtained), is considered TRD. In another embodiment, the compositions, methods and pharmaceutical packs of the invention are further advantageous in subjects failing to achieve treatment remission (which may be defined as a score of <7 according to the MADRS scale).

In some embodiments, the subject has been determined as being resistant to two or more (e.g. 2-5) different antidepressants, or, in other embodiments, to two or more distinct classes of antidepressants (such as SSRIs, SNRIs, tricyclic antidepressants, MAO inhibitors and 5-$HT_2$ blockers). In other embodiments, the subject has been determined as being resistant to treatment with at least one SSRI and/or SNRI as disclosed herein, wherein each possibility represents a separate embodiment of the invention. According to exemplary embodiments, said subject is resistant to treatment with at least one of citalopram, escitalopram, sertraline, mirtazapine, and combinations thereof, wherein each possibility represents a separate embodiment of the invention.

In another embodiment, the subject to be treated manifests at least one and typically a plurality of depressive and/or anxiety symptoms, characteristic of a disorder as disclosed herein. For example, DSM-5 requires five or more depressive symptoms as defined therein to be present during the same two-week period that are a change from previous functioning in order to define MDD (wherein depressed mood and/or loss of interest/pleasure must be present, and symptoms attributable to another medical condition are excluded). In another embodiment, the methods of the invention are used for preventing or treating depressive and/or anxiety symptoms. In another embodiment the subject is at risk for developing a depressive and/or anxiety disorder, e.g. MDD or TRD. In another embodiment the method is used for preventing or inhibiting post-stroke depression.

According to certain embodiments, disorders associated with depressive symptoms include, but are not limited to, major depressive disorder, unipolar major depressive disorder, dysthymic disorder, treatment-resistant depression, bipolar depression, bipolar disorder with mixed features, adjustment disorder with depressed mood, cyclothymic disorder, atypical depression, seasonal affective disorder, melancholic depression, psychotic depression, post schizophrenic depression, schizoaffective disorder-depressed type, depression due to general medical condition, post stroke depression, and chronic fatigue syndrome, wherein each possibility represents a separate embodiment of the invention. In another embodiment, disorders associated with anxiety symptoms may be posttraumatic stress disorder, acute stress disorder, adjustment disorder, bereavement related disorder, generalized anxiety disorder (GAD), social anxiety disorder, panic disorder, obsessive compulsive disorder (OCD), and anxiety disorder due to a medical condition, wherein each possibility represents a separate embodiment of the invention. Such symptoms and conditions are readily recognized by the skilled artisan using acceptable criteria such as DSM-5 definitions and diagnostic criteria.

In another embodiment the subject is diagnosed with white matter lesions (WMLs), namely histopathologic changes associated with incidental white matter signal hyperintensities on magnetic resonance imaging (MRI), prior to treatment. In another embodiment, the subject is diagnosed with mild WMLs load (evaluated by grading scale 1) on the Fazekas score (Fazekas F, et al., 1987, AJR Am J Roentgenol; 149(2):351-6, Fazekas F, et al., 1993, Neurology 43(9), 1683-9), characterized by punctate foci of hyperintense signals in deep white matter. In another embodiment, the subject is diagnosed with moderate WML load (evaluated by grading scale 2) on the Fazekas score, characterized by beginning confluence of foci of hyperintense signals in deep white matter. In another embodiment, the subject is diagnosed with mild to moderate WMLs load (evaluated by grading scale 1-2) on the Fazekas score. In another embodiment said subject is diagnosed with severe WMLs load (evaluated by grading scale 3) on the Fazekas score, characterized by large confluent areas of hyperintense signals in deep white matter. In another embodiment said subject is diagnosed with moderate to severe WMLs load (evaluated by grading scale 2-3) on the Fazekas score. Each possibility represents a separate embodiment of the invention.

In another embodiment, the subject is diagnosed with a recent stroke (e.g. within two years from stroke occurrence). In another embodiment, the subject has been diagnosed with stroke (cerebral infarction or transient ischemic attack) 1-12 months, 3-24 months, 4-24 months, 3-36 months or 4-36 months prior to treatment (administration of the maraviroc or derivative thereof), wherein each possibility represents a separate embodiment of the invention. In another embodiment, the subject is further diagnosed with depression and/or anxiety within 1-12, 3-24, or 4-24 months following stroke occurrence. In another embodiment, said subject has been diagnosed with cerebral infarction or transient ischemic attack 4-36 months prior to administration of the maraviroc or derivative thereof and further diagnosed with depression and/or anxiety within 24 months following stroke occurrence. Each possibility represents a separate embodiment of the invention.

In another embodiment, the subject has been diagnosed with PSD, defined as a depressive disorder that was not existent before a stroke and occurred in chronological context thereto. Significant worsening of existing depressive symptoms after a stroke, in a manner associated with the occurrence of anatomical neurovascular lesions (measurable e.g. by neuroimaging such as MM or CT), are further encompassed in some embodiments. In the context of the present invention, PSD includes in particular new onset MDD diagnosed within two years of the stroke.

Additionally or alternatively, the subject has been diagnosed with PSA, defined as an anxiety disorder that was not existent before a stroke and occurred in chronological context thereto. Significant worsening of existing anxiety symptoms after a stroke, in a manner associated with the occurrence of anatomical neurovascular lesions (measurable e.g. by neuroimaging such as MM or CT), are further encompassed in some embodiments. Anxiety symptoms manifested by PSA patients are often contextually related to the stroke (e.g. related to fear of stroke re-occurrence). In the context of the present invention, PSA represents in particular new onset anxiety diagnosed within two years of the stroke.

Gold standard for the diagnosis of depression and anxiety represents the DSM-IV and DSM-5 criteria. In addition, several diagnostic tests are available and may conveniently be used by the skilled artisans to diagnose and continuously evaluate the related symptoms in a quantitative manner (e.g. for easy assessment of therapeutic success). For example, the Montgomery-Asberg Depression Rating Scale (MADRS), the Quick Inventory of Depressive Symptomatology—Self Report (QIDS-SR16) scale, the Geriatric depression scale (GDS) and the clinical global impression (CGI) scales may be used in the assessment and quantification of depression, as exemplified herein, along with other available scales such as the Hamilton rating scale of depression (HAMD) and the Beck Depression Inventory (BDI). Anxiety scales including, but not limited to, the Generalized Anxiety Disorder 7-item Scale (GAD-7, which measures severity of anxiety), the state-trait anxiety inventory-severity (STAI-S, measuring state anxiety, or anxiety about an event, e.g. stroke), and the post-traumatic stress disorder (PTSD) checklist specific for a stressor (PCL-S, a 17-item scale that corresponds to the DSM-IV criteria for PTSD, e.g. using the stressor "stroke), may be used in the assessment and quantification of anxiety. In a particular embodiment, the subject has been diagnosed with moderate to severe anxiety as determined by the GAD-7 scale (for example, moderate anxiety manifested as GAD-7 of 10-14 or severe anxiety manifested as GAD-7 of 15-21).

In some embodiments, the compositions and methods of the invention are also particularly suitable for use in patients for whom a fast treatment onset is beneficial, including, but not limited to, patients at risk of self-harm. Accordingly, in another embodiment the subject is at high risk of suicidal behavior evaluated by the Columbia Suicide Severity Rating Scale (C-SSRS).

According to additional or alternative embodiments, the subject is afflicted with post-stroke cognitive impairment (PSCI), defined as failure in one or more cognitive domains developing after stroke (e.g. executive function, memory, language, visuospatial ability, visuoconstructional ability, and/or global cognitive function). Significant worsening of cognitive impairment after a stroke, wherein the pace of deterioration exceeds the expected rate for the respective age group, is further encompassed in some embodiments. PSCI includes mild and major neurocognitive disorders (which may be assessed according to DSM-IV or DSM-5 criteria) that are related (and generally considered consequent) to an acute cerebrovascular event. In some embodiments, the subject has been diagnosed with established PSCI, in which the onset of the cognitive deficit has been determined to be temporally related to one or more acute cerebrovascular events as disclosed herein, with persisting symptoms beyond the acute recovery phase. In the context of the present invention, PSCI includes in particular patients in which the onset of the cognitive deficit has been determined to be temporally related to the stroke, with presence of neuroimaging evidence, such as by MRI or CT, of a cerebrovascular disease, and wherein and the symptoms of said cognitive deficit are present beyond three months from the onset of the stroke. In some embodiments, the cognitive impairment may conveniently be assessed and quantified by cognitive tests including, but not limited to the Montreal Cognitive Assessment (MoCA), the Toronto Cognitive Assessment (TorCA), the Clinical Dementia Rating (CDR), and the repeatable computerized battery of cognitive tests (Neurotrax). In other embodiments, more generalized tests for cognitive performance, such as the Mini-mental state examination (MA/ISE) and the Alzheimer's Disease Assessment Scale-Cognitive Sub scale (ADAS-Cog), may conveniently be used. In a particular embodiment, the subject has been diagnosed with a mild to moderate impairment, characterized by MoCA scores of 20-25 or 17-25, respectively (along with subjective cognitive complaints, and without substantial loss of function). In yet another embodiment, the subject is not concomitantly afflicted with cognitive impairment, e.g. dementia, mild cognitive impairment (MCI) or PSCI, wherein each possibility represents a separate embodiment of the invention.

In another embodiment, the subject is not amenable for treatment with one or more antidepressants due to tolerability or safety issues (for example, SSRI- and/or SNRI-related side effects). In another embodiment the subject is not concurrently afflicted with an additional disorder selected from the group consisting of an HIV infection, a neurodegenerative disorder, a cardiovascular disorder, and an inflammatory disorder, wherein each possibility represents a separate embodiment of the invention. In another embodiment, the subject is a carrier of a CCR5-Δ32 allele. In another embodiment the subject is not a carrier of a CCR5-Δ32 allele. In another embodiment, the subject is not concomitantly afflicted with hypertension, diabetes mellitus or hyperlipidemia, wherein each possibility represents a separate embodiment of the invention.

Pharmaceutical Compositions and Kits

According to certain aspects and embodiments, the invention relates to (or employs the use of) a pharmaceutical composition comprising a therapeutically effective amount of at least one active ingredient as disclosed herein (e.g. a CCR5 antagonist or inhibitor and/or an antidepressant), and a pharmaceutically acceptable carrier or excipient.

Suitable pharmaceutically acceptable carriers or excipients include, but are not limited to, a binder, a filler, a diluent, a surfactant or emulsifier, a glidant or lubricant, buffering or pH adjusting agent, a tonicity enhancing agent, a wetting agent, a preservative, an antioxidant, a flavoring agent, a colorant, and a mixture or combination thereof. Each possibility represents a separate embodiment. Suitable binders include, but are not limited to, polyvinylpyrrolidone, copovidone, hydroxypropyl methylcellulose, starch, and gelatin. Each possibility represents a separate embodiment. Suitable fillers include, but are not limited to, sugars such as lactose, sucrose, mannitol or sorbitol and derivatives therefore (e.g. amino sugars), ethylcellulose, microcrystalline cellulose, and silicified microcrystalline cellulose. Each possibility represents a separate embodiment. Suitable lubricants include, but are not limited to, sodium stearyl fumarate, stearic acid, polyethylene glycol or stearates, such as magnesium stearate. Each possibility represents a separate embodiment. Suitable diluents include, but are not limited to, dicalcium phosphate dihydrate, sugars, lactose, calcium phosphate, cellulose, kaolin, mannitol, sodium chloride, and dry starch. Each possibility represents a separate embodiment.

Suitable surfactants or emulsifiers include, but are not limited to, polyvinyl alcohol (PVA), polysorbate, polyethylene glycols, polyoxyethylene-polyoxypropylene block copolymers known as "poloxamer", polyglycerin fatty acid esters such as decaglyceryl monolaurate and decaglyceryl monomyristate, sorbitan fatty acid ester such as sorbitan monostearate, polyoxyethylene sorbitan fatty acid ester such as polyoxyethylene sorbitan monooleate (Tween), polyethylene glycol fatty acid ester such as polyoxyethylene monostearate, polyoxyethylene alkyl ether such as polyoxyethylene lauryl ether, polyoxyethylene castor oil and hardened castor oil such as polyoxyethylene hardened castor oil. Each possibility represents a separate embodiment.

Suitable glidants or lubricants include, but are not limited to, colloidal silicon dioxide, magnesium stearate, talc, and mineral oil. Each possibility represents a separate embodiment. Suitable buffering or pH adjusting agents include, but are not limited to, acidic buffering agents such as short chain fatty acids, citric acid, acetic acid, hydrochloric acid, sulfuric acid and fumaric acid; and basic buffering agents such as tris, sodium carbonate, sodium bicarbonate, sodium hydroxide, potassium hydroxide, and magnesium hydroxide. Each possibility represents a separate embodiment. Suitable tonicity enhancing agents include, but are not limited to, ionic and non-ionic agents such as, alkali metal or alkaline earth metal halides, urea, glycerol, sorbitol, mannitol, propylene glycol, and dextrose. Each possibility represents a separate embodiment. Suitable wetting agents include, but are not limited to, glycerin, cetyl alcohol, and glycerol monostearate. Each possibility represents a separate embodiment. Suitable preservatives include, but are not limited to, benzalkonium chloride, benzoxonium chloride, thiomersal, phenylmercuric nitrate, phenylmercuric acetate, phenylmercuric borate, methylparaben, propylparaben, chlorobutanol, benzyl alcohol, phenyl alcohol, chlorohexidine, and polyhexamethylene biguanide. Each possibility represents a separate embodiment.

Suitable antioxidants include, but are not limited to, sorbic acid, ascorbic acid, ascorbate, glycine, α-tocopherol, butylated hydroxyanisole (BHA), and butylated hydroxytoluene (BHT). Each possibility represents a separate embodiment. Suitable flavoring agents include, but are not limited to, sweeteners such as sucralose and synthetic flavor oils and flavoring aromatics, natural oils, extracts from plants, leaves, flowers, and fruits, and combinations thereof. Exemplary flavoring agents include cinnamon oils, oil of wintergreen, peppermint oils, clover oil, hay oil, anise oil, *eucalyptus*, vanilla, citrus oil such as lemon oil, orange oil, grape and grapefruit oil, and fruit essences including apple, peach, pear, strawberry, raspberry, cherry, plum, pineapple, and apricot. Each possibility represents a separate embodiment. Suitable colorants include, but are not limited to, alumina (dried aluminum hydroxide), annatto extract, calcium carbonate, canthaxanthin, caramel, β-carotene, cochineal extract, carmine, potassium sodium copper chlorophyllin (chlorophyllin-copper complex), dihydroxyacetone, bismuth oxychloride, synthetic iron oxide, ferric ammonium ferrocyanide, ferric ferrocyanide, chromium hydroxide green, chromium oxide greens, guanine, mica-based pearlescent pigments, pyrophyllite, mica, dentifrices, talc, titanium dioxide, aluminum powder, bronze powder, copper powder, and zinc oxide. Each possibility represents a separate embodiment.

In certain aspects and embodiment, the pharmaceutical composition of the present invention is formulated as tablet, pill, capsule (e.g. soft or hard gelatin capsule), pellets, granules, powder, a wafer, coated or uncoated beads, lozenge, sachet, cachet, elixir, an osmotic pump, a depot system, an iontophoretic system, a patch, suspension, dispersion, emulsion, solution, syrup, aerosol, oil, ointment, suppository, a gel, and a cream. Each possibility represents a separate embodiment.

For preparing solid compositions such as tablets, the active pharmaceutical ingredient is mixed with a pharmaceutical carrier or excipient to form a solid pre-formulation composition containing a substantially homogeneous distribution of the compound of the present invention in the pharmaceutical carrier or excipient.

Any method can be used to prepare the pharmaceutical compositions. For example, solid dosage forms can be prepared by wet granulation, dry granulation, direct compression and the like as is known in the art. The liquid forms in which the compositions of the present invention may be incorporated, for administration via oral administration or by injection or another parenteral route, include aqueous solutions, suitably flavored syrups, aqueous or oil suspensions, and flavored emulsions with edible oils such as cottonseed oil, sesame oil, coconut oil, or peanut oil, as well as elixirs and similar pharmaceutical vehicles. Each possibility represents a separate embodiment.

In some embodiments, the active ingredient is a CCR5 inhibitor or antagonist. As used herein, the term antagonist (e.g. CCR5 antagonist) refers to a compound that specifically binds to the target molecule (e.g. receptor), and downregulates its activity (either by blocking the ligand-binding site or allosterically). For example, maraviroc is a negative allosteric modulator of the CCR5 receptor. In other embodiments, the use of other CCR5 inhibitors, specifically designed to downregulate the activity or expression of CCR5, is contemplated.

In another embodiment, the CCR5 inhibitor or antagonist is maraviroc (or a derivative thereof). In another embodiment, the CCR5 inhibitor or antagonist is cenicriviroc. In another embodiment, the inhibitor may be e.g. a CCR5-specific double-stranded RNA (capable of downregulating CCR5 expression), a compound antagonizing the binding of CCR5 to its ligand (e.g. small molecule antagonist), a neutralizing antibody to CCR5, an isolated peptide derived from the sequences of CCR5 or analogs thereof capable of inhibiting CCR5, a CCR5-specific antisense nucleic acid, a CCR5-specific antagonist microRNA, a CCR5-specific silencing RNA molecule and a CCR5-specific enzymatic RNA molecule. Each possibility represents a separate embodiment of the invention.

In a particular embodiment, the active ingredient is maraviroc, which may be formulated e.g. for oral administration in a unit dosage form such as a tablet or a capsule. According to exemplary embodiments, maraviroc may be present in the dosage form at therapeutically effective doses as disclosed herein. In a particular embodiment, said oral unit dosage form may contain e.g. 150 mg or 300 mg maraviroc.

In another embodiment, the active ingredient is an antidepressant, which may be prescribed to a patient for the treatment of depression. Pharmaceutical agents commonly indicated for treating depression and alleviating depressive symptoms typically regulate the balance of neurotransmitter effectors of mood disorders (e.g. serotonin, norepinephrine or dopamine), and may be categorized according to their target selectivity (e.g. SSRIs, SNRIs, monoamine oxidase inhibitors (MAO-I), and 5-$HT_2$ blockers) and chemical structure (e.g. unicyclic, tricyclic, tetracyclic, and heterocyclic antidepressants).

For example, SSRIs are inhibitors of the monoamine transporters, which have stronger inhibitory effect at the serotonin transporter than the dopamine and the noradrenaline transporters, and prevent reuptake of serotonin (5-hydroxytryptamine [5-HT]). By preventing reuptake of 5-HT presynaptically, SSRIs result in more 5-HT to stimulate postsynaptic 5-HT receptors. SSRIs are selective to the 5-HT system but not specific for the different 5-HT receptors. They stimulate 5-$HT_1$ receptors, with antidepressant and anxiolytic effects, but they also stimulate 5-$HT_2$ receptors, commonly causing anxiety, insomnia, and sexual dysfunction, and 5-$HT_3$ receptors, commonly causing nausea and headache. Thus, SSRIs can paradoxically relieve and cause anxiety. According to some embodiments, exemplary SSRIs used in compositions, methods, kits and pharmaceutical packs of the invention include, but are not limited to, citalopram, (S)-citalopram, escitalopram, fluoxetine, fluvoxamine, paroxetine, sertraline, dapoxetine and pharmaceutically acceptable salts thereof, wherein each possibility represents a separate embodiment of the invention. In a particular embodiment, said SSRI is citalopram (or an enantiomer thereof such as escitalopram).

5-$HT_2$ blockers (e.g. trazodone, mirtazapine) block primarily the 5-$HT_2$ receptor and inhibit reuptake of 5-HT and norepinephrine. For example, mirtazapine inhibits 5-HT reuptake and blocks alpha-2 adrenergic autoreceptors, as well as 5-HT2 and 5-HT3 receptors. The drug may cause sedation and weight gain, mediated by $H_1$ (histamine) blockade, while trazodone may cause orthostatic (postural) hypotension and is very sedating, so its use in antidepressant doses (>200 mg/day) is limited.

SNRIs (e.g., desvenlafaxine, duloxetine, levomilnacipran, venlafaxine, vortioxetine) have a dual 5-HT and norepinephrine mechanism of action, as do tricyclic antidepressants. Their toxicity approximates that of SSRIs, wherein nausea is the most common problem during the first 2 weeks, and dose-dependent increases in blood pressure (BP) may occur with high doses.

Heterocyclic antidepressants include tricyclic (tertiary amines amitriptyline and imipramine and their secondary amine metabolites nortriptyline and desipramine), modified tricyclic, and tetracyclic antidepressants. Acutely, heterocyclic antidepressants increase the availability of primarily norepinephrine and, to some extent, 5-HT by blocking reuptake in the synaptic cleft. Long-term use downregulates alpha-1 adrenergic receptors on the postsynaptic membrane—a possible final common pathway of their antidepressant activity. Although effective, these drugs are now rarely used because overdose causes toxicity and they have more adverse effects than other antidepressants. TCA include, for example, imipramine, amitriptyline, desipramine, nortriptyline, doxepin, protriptyline, trimipramine, chlomipramine, and amoxapine.

MAO-I (e.g. phenelzine, tranylcypromine, and moclobemide) inhibit the oxidative deamination of the 3 classes of biogenic amines (norepinephrine, dopamine, 5-HT) and other phenylethylamines. MAOIs are used infrequently due to safety concerns, in particular when ingested concurrently with a sympathomimetic drug or food containing tyramine or dopamine.

In addition, certain atypical antidepressants, such as bupropion and vortioxetine, have been approved for clinical use. Bupropion is a norepinephrine-dopamine reuptake inhibitor that favorably influences catecholaminergic, dopaminergic, and noradrenergic function and does not affect the 5-HT system. Bupropion may cause hypertension and/or seizures in some patients, wherein the risk of stroke is dose-dependent increased in patients with bulimia.

According to exemplary embodiments, the active ingredient to be used in combination with maraviroc may be e.g. escitalopram, sertraline, mirtazapine, pregabalin, or combinations thereof.

According to embodiments of the invention, salts, enantiomers and chemical derivatives of drug compounds referred to herein may be used, as long as they retain the required therapeutic properties and considered equivalents thereto. The term "derivative" as used herein in connection to an active ingredient refers to conservative derivatization that may be performed at permissive sites of the molecule, such that its biological activity and toxicity properties are not substantially altered. For example, the triazole ring of maraviroc may be derivatized for linkage to macromolecules (e.g. for the purpose of extending its circulating serum half-life) without significant loss of activity. Structure-function considerations for maraviroc and citalopram derivatization have been disclosed e.g. by Asano et al. (ACS Med Chem Lett. 2014 Feb. 13; 5(2): 133-137) and Larsen et al. (Br J Pharmacol. 2016; 173(5):925-936. doi:10.1111/bph.13411), respectively. In another example, citalopram enantiomers that are available for clinical use in the treatment of depressive disorders include (S)-citalopram or escitalopram. Such enantiomers are considered to correspond to the activity of the citalopram racemate (with the required dose correction for using the active enantiomer rather than the racemate), while the (R)-stereoisomer (R-citalopram) is not considered to have useful effects for treating depression.

In another aspect, there is provided a pharmaceutical composition comprising i) maraviroc or a derivative thereof, ii) a SSRI and iii) optional pharmaceutically acceptable carriers, excipients or diluents. In another aspect, there is provided a pharmaceutical composition comprising i) maraviroc, ii) a SSRI and iii) optional pharmaceutically acceptable carriers, excipients or diluents, the maraviroc and SSRI provided at amounts effective to treat or prevent the appearance of depressive and/or anxiety symptoms in a subject in need thereof. In another embodiment, the SSRI is citalopram, or a derivative (or enantiomer) thereof. In another embodiment, the SSRI is citalopram or escitalopram. In another embodiment the SSRI is selected from the group consisting of citalopram, escitalopram, sertraline, and combinations thereof. In another embodiment, said composition consists of maraviroc and citalopram as active ingredients. In another embodiment, said composition consists of maraviroc and escitalopram as active ingredients. In another embodiment, said composition consists of maraviroc and sertraline as active ingredients. In another embodiment, the composition comprises a CCR5 inhibitor or antagonist and a SSRI that are provided at amounts effective to treat or prevent depressive and anxiety symptoms in a subject in need thereof. In another embodiment, the composition is formulated for oral administration. It is to be understood, that known combinations as described herein, such as those disclosed in US 2008021038 (piperidine/8-azabicyclo [3.2.1.] octan derivatives) are explicitly excluded.

In another aspect, the invention provides kits and pharmaceutical packs, useful for the treatment and prevention of depressive and/or anxiety disorders. In another embodiment there is provided a pharmaceutical pack, comprising: i) a first pharmaceutical composition comprising maraviroc or a derivative thereof, ii) a second pharmaceutical composition comprising at least one SSRI. In another embodiment there is provided a pharmaceutical pack, comprising: i) a first pharmaceutical composition comprising maraviroc, ii) a second pharmaceutical composition comprising at least one SSRI, the maraviroc and SSRI provided at amounts effective to treat or prevent the appearance of depressive and/or anxiety symptoms in a subject in need thereof. In another embodiment the SSRI is citalopram (or a derivative or enantiomer thereof). In another embodiment, the SSRI is citalopram or escitalopram. In another embodiment the at least one SSRI is selected from the group consisting of citalopram, escitalopram, and sertraline. In another embodiment, said pharmaceutical pack consists of maraviroc and citalopram as active ingredients. In another embodiment, said pharmaceutical pack consists of maraviroc and escitalopram as active ingredients. In another embodiment, said pharmaceutical pack consists of maraviroc and sertraline as active ingredients. In another embodiment, the pharmaceutical pack comprises a CCR5 inhibitor or antagonist and a SSRI that are provided at amounts effective to treat or prevent depressive and anxiety symptoms in a subject in need thereof. In another embodiment, the pack further comprises instructions for administering the first and second pharmaceutical compositions in concurrent or sequential combination to a subject in need thereof, such as a subject in need of treatment of a depressive and/or anxiety disorder (e.g. TRD), as disclosed herein.

In another embodiment, there is provided a kit, comprising i) maraviroc or a derivative thereof, ii) instructions for administering the maraviroc or derivative thereof in concurrent or sequential combination with a SSRI to a subject in need thereof, such as a subject in need of treatment of a depressive and/or anxiety disorder (e.g., TRD), as disclosed herein. In another embodiment, the SSRI is citalopram (or a derivative thereof).

Therapeutic Uses and Regimens

In another embodiment, the methods of the invention comprise administering to the subject an effective amount of a CCR5 inhibitor or antagonist. In another embodiment, the inhibitor is maraviroc (or a derivative thereof). In another embodiment, the CCR5 inhibitor or antagonist is cenicriviroc. In another embodiment, the inhibitor of CCR5 used in compositions, methods, kits and pharmaceutical packs of the invention may be e.g. a double-stranded RNA, a compound antagonizing the binding of CCR5 to its ligand (e.g. small molecule antagonist), a neutralizing antibody to CCR5, an isolated peptide derived from the sequences of CCR5 or analogs thereof capable of inhibiting CCR5, an antisense nucleic acid, an antagonist microRNA, a silencing RNA molecule and an enzymatic RNA molecule. Each possibility represents a separate embodiment of the invention. In a particular embodiment, the small molecule antagonist is maraviroc.

According to advantageous embodiments, the methods of the invention comprise administering to a subject in need thereof a pharmaceutical composition comprising a therapeutically effective amount of maraviroc or a derivative thereof, more typically maraviroc. As used herein, a therapeutically effective amount is an amount effective to treat, inhibit, ameliorate or reverse one or more symptoms of the disorder to be treated (e.g. a depressive and/or anxiety disorder as disclosed herein or PSCI).

In another embodiment, the maraviroc is administered at a therapeutically effective amount as disclosed herein. For example, maraviroc may be administered in the methods of the invention at a daily dose of about 10-600 mg, e.g. 100-300, 100-250, 75-150, 100-150, 125-250, 75-300, 150-600 or any integer in between. In a particular embodiment, said maraviroc may be used in a 150 mg unit dosage form administered once daily. In other embodiments of the methods of the invention, said maraviroc may be used in a 300 or 600 mg unit dosage form, e.g. administered once daily. In other embodiments of the methods of the invention, said maraviroc may be used in a 150 mg or 300 mg unit dosage form, e.g. administered twice daily. In certain exemplary embodiments, therapeutically effective amounts to be used in various methods, compositions and pharmaceutical packs of the invention, may range between about 150 mg and about 600 mg per day, or include about 150 mg to about 600 mg, respectively.

In another embodiment, maraviroc treatment is given for at least two weeks and typically for 4-10 weeks or more, e.g. for 1-3 months, or so long as the symptoms (e.g. of a depressive and/or anxiety disorder as disclosed herein) are ameliorated or disappear. In various exemplary embodiments, the treatment regimen comprises oral administration of maraviroc once daily at an effective amount for 4, 5, 6, 7, 8, 9 or 10 weeks or more, wherein each possibility represents a separate embodiment of the invention. According to non-limitative examples, maraviroc may be administered at an effective amount of 100-600 mg, typically 150-300 mg once daily for the treatment of a depressive and/or anxiety disorder as disclosed herein, and 150-300 mg once or twice daily (e.g. to a total dose of 600 mg) for the treatment of established PSCI, wherein each possibility represents a separate embodiment of the invention.

In another embodiment, the CCR5 inhibitor (e.g. maraviroc) is administered in combination with at least one antidepressant. In some embodiments, the antidepressant is selected from the group consisting of SSRIs, Serotonin-Norepinephrine Reuptake Inhibitors (SNRIs), and tricyclic antidepressants (TCAs). In another embodiment, the antidepressant is a SSRI. According to some embodiments, exemplary SSRI used in compositions, methods, kits and pharmaceutical packs of the invention include, but are not limited to, citalopram, (S)-citalopram, escitalopram, fluoxetine, fluvoxamine, paroxetine, sertraline, dapoxetine and pharmaceutically acceptable salts thereof, wherein each possibility represents a separate embodiment of the invention. In a particular embodiment, said SSRI is citalopram (or an enantiomer thereof such as escitalopram).

According to exemplary embodiments, the methods of the invention comprise administering to said subject maraviroc in combination with citalopram, escitalopram, sertraline, mirtazapine, or combinations thereof, wherein each possibility represents a separate embodiment of the invention. In some embodiments, maraviroc is administered to the subject in combination of a plurality of antidepressants. As disclosed and demonstrated herein, maraviroc may advantageously be used in combination with multiple drugs (e.g. antidepressants and anti-anxiety drugs) and achieve remarkable therapeutic efficacy without impairing tolerability. For instance, as exemplified herein, maraviroc may be used in combination with the SSRI escitalopram and a second SSRI such as Sertraline, or a second drug which is a SNRI or another antidepressant such as Mirtazapine, to overcome TRD and in particular in patients following stroke while minimizing adverse effects. In yet other embodiments, maraviroc may further be administered in combination with other antidepressants and anxiety-modulating drugs such as pregabalin. Thus, according to non-limitative examples, embodiments of the invention relate to the use of the following exemplary combinations: maraviroc, escitalopram and mirtazapine, maraviroc, escitalopram and pregabalin, and maraviroc, escitalopram and sertraline, wherein each possibility represents a separate embodiment of the invention.

Suitable doses and treatment regimens of antidepressants (e.g. SSRIs) include, without limitation, 20-40 mg/day citalopram (starting dose 20 mg once/day), 10-20 mg/day escitalopram (starting dose 10 mg once/day), 20-60 mg/day fluoxetine (starting dose 10 mg once/day), 50-200 mg/day sertraline (starting dose 50 mg once/day), 15-45 mg/day mirtazapine (starting dose 15 mg once/day), 100-200 mg/day fluvoxamine (starting dose 50 mg once/day), 20-60 mg/day paroxetine (starting dose 20 mg once/day; or 25-62.5 mg Paroxetine CR, starting dose 25 mg once/day). In some embodiments, maraviroc combination therapy allows the treatment (e.g. SSRI) dose to be reduced (e.g. by 10%, 20%, 30, 40% or 50%), thereby enhancing tolerability without impairing efficacy.

In another embodiment, the inhibitor is not administered in combination with an additional anti-retroviral agent. In another embodiment, the inhibitor (or the combination of CCR5 inhibitor and SSRI) is not administered in combination with additional drugs such as those indicated for the treatment of HIV infection, neurodegenerative disorders, cardiovascular disorders, and inflammatory disorders. Each possibility represents a separate embodiment of the invention. In another embodiment, the CCR5 inhibitor (e.g. maraviroc) is administered as a sole active ingredient.

In another aspect, the invention provides a method for enhancing the efficacy of an antidepressant treatment, comprising administering the treatment in concurrent or sequential combination with maraviroc or a derivative thereof, thereby enhancing the efficacy of the antidepressant treatment. In another embodiment the antidepressant treatment is a SSRI. In another embodiment, enhancing the efficacy of the antidepressant treatment comprises providing a more rapid onset of therapeutic efficacy (shortening the treatment lag).

For example, the average time to initial response (onset) in common antidepressants is typically about 4-6 weeks and up to about 8 weeks from initial treatment. According to some embodiments of the invention, this time lag may be shortened by at least 30% and typically by 50%, 60%, 70% or 80%. In other embodiments, the treatment lag may be shortened by at least one week and typically by 2, 3, 4 or 5 weeks or more. For example, the treatment lag may be shortened in embodiments of the invention to up to 1-2 weeks.

In another embodiment, enhancing the efficacy of treatment refers to improving the depressive score, e.g. by at least 25%, 40%, 50%, 60%, 75%, 80% and up to 100%, as evaluated e.g. by the MADRS scale. For example, as demonstrated herein, when supplemented to an existing antidepressant treatment which provided no therapeutic response, a significant, marked response was observed in all patients following maraviroc supplementation.

In some embodiments, the compositions and methods of the invention are used for treating or inhibiting symptoms of a depressive and/or anxiety disorder as disclosed herein, wherein each possibility represents a separate embodiment of the invention. For example, without limitation, several symptoms of depression manifested after stroke have been examined in particular in different studies. Anhedonia, defined as the inability to enjoy normally enjoyable activities was reported to be correlated with stroke lesion volume in the parahippocampal gyms. Apathy as symptom of depression defined as "an absence or a decrease in motivations, interests, and emotions, which cannot be ascribed to a lack of consciousness, cognitive impairment, or emotional distress" was also addressed, and an association between apathy and right hemispheric stroke in the basal ganglia was suggested. A differentiation between affective-depressive and apathetic subtypes of PSD was suggested. In various embodiments, inhibition of symptoms refers to reduction in the number and/or intensity of symptoms, wherein each possibility represents a separate embodiment of the invention. Conveniently, reduction in depressive and anxiety symptoms may be assessed and quantified by reduction in depressive and anxiety scores, respectively, as disclosed herein.

In another embodiment, the compositions and methods of the invention provide a reduction of at least 30% and typically of 40% to 80% in depressive scores as evaluated by the MADRS scale within 2-10 weeks of treatment (or of 60-80% within 4-10 weeks of treatment). In another embodiment the compositions and methods of the invention provide remission of the depressive and/or anxiety disorder. In a particular embodiment the remission is obtained within 10 weeks of treatment.

In another embodiment the compositions and methods of the invention are used for treating PSCI in a subject diagnosed with established PSCI. In one embodiment, treating comprises improving the cognitive score of the subject compared to the score determined prior to treatment. In another embodiment, treating comprises improving in 2 points the cognitive score of said subject compared to the score determined prior to treatment. In a particular embodiment the score is determined based on the Montreal Cognitive Assessment (MoCA). In another embodiment treating comprises eliminating or reducing the severity of a symptom or clinical sign associated with PSCI compared to its level as determined prior to treatment.

The following examples are presented in order to more fully illustrate some embodiments of the invention. They should, in no way be construed, however, as limiting the broad scope of the invention.

EXAMPLES

Example 1. CCR5-Δ32 in Post-Stroke Depression and in Post-Stroke Anxiety

The role of CCR5 in depression and anxiety was investigated in post-stroke patients carrying the CCR5-Δ32 mutation and having or not having depressive and anxiety symptoms in a prospective stroke cohort. The cohort was an observational analysis of the long-term outcome in mild to moderate first-ever ischemic stroke, with comprehensive data from hospitalization and follow-up, including 3T MRI, thorough cognitive and psychological assessments, plasma, serum and DNA samples. This cohort was screened for the CCR5-Δ32 (rs333) mutation. Out of 435 patients studied, 70 patients (16.1%) were carriers of CCR5 Δ32 mutation. 85.7% of the carriers were Ashkenazi in their origin, compared to 51.9% in non-carriers, as would be expected with the genetic association of this mutation (more frequent in Ashkenazi Jewish).

As shown in FIG. 1A, CCR5-Δ32 carriers presented fewer depressive symptoms (lower general depressive score (GDS)) at hospital admission, as well as 6, 12 and 24 months after the stroke event, compared with non-carriers ($p=0.035$, $p<0.001$, $p<0.001$, $p=0.006$, respectively). The association of the CCR5-Δ32 with GDS scores at 6 and 12 months remained significant after adjustment for age, gender, education, administration of SSRIs or SNRIs during the follow-up period, ethnicity, and the existence of cortical infarcts (Table 1).

TABLE 1

| GDS scores | | | | | | |
|---|---|---|---|---|---|---|
| | Model 1 β | SE | P | Model 2 β | SE | P |
| GDS at admission | −0.081 | 0.357 | 0.093 | — | — | — |
| GDS at 6 months | −0.149 | 0.490 | 0.011 | −0.120 | 0.486 | 0.029 |
| GDS at 12 months | −0.171 | 0.506 | 0.003 | −0.130 | 0.495 | 0.023 |
| GDS at 24 months | −0.130 | 0.556 | 0.033 | −0.078 | 0.549 | 0.195 |

GDS, geriatric depression scale; SE, standard error.

Figure 1B:
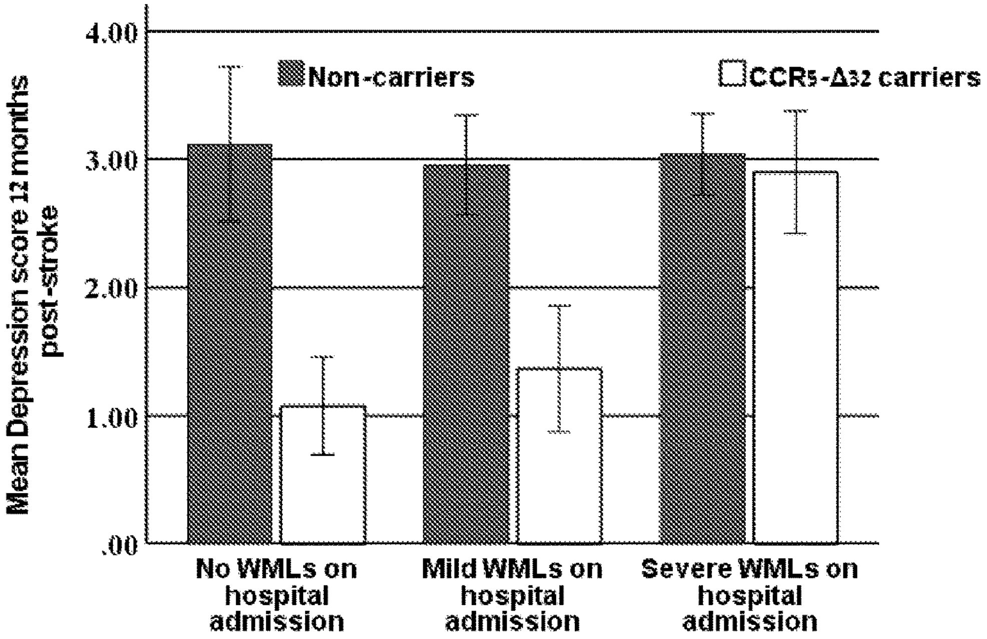

The post-stroke patients were categorized to groups according to their degree of white-matter lesions (WMLs) as determined by MM on hospital admission: No WMLs, mild WMLs, and severe WMLs. FIG. 1B shows that CCR5-Δ32 carriers who did not have WMLs or those who had mild WMLs on hospital admission manifested one year after stroke significantly less depressive symptoms than non-carriers who had no WMLs or mild WMLs, respectively. Interestingly, CCR5-Δ32 carriers who had severe WMLs on hospital admission also showed one year after the stroke event less depressive symptoms than the non-carriers having severe WMLs (FIG. 1B).

Figure 1C:
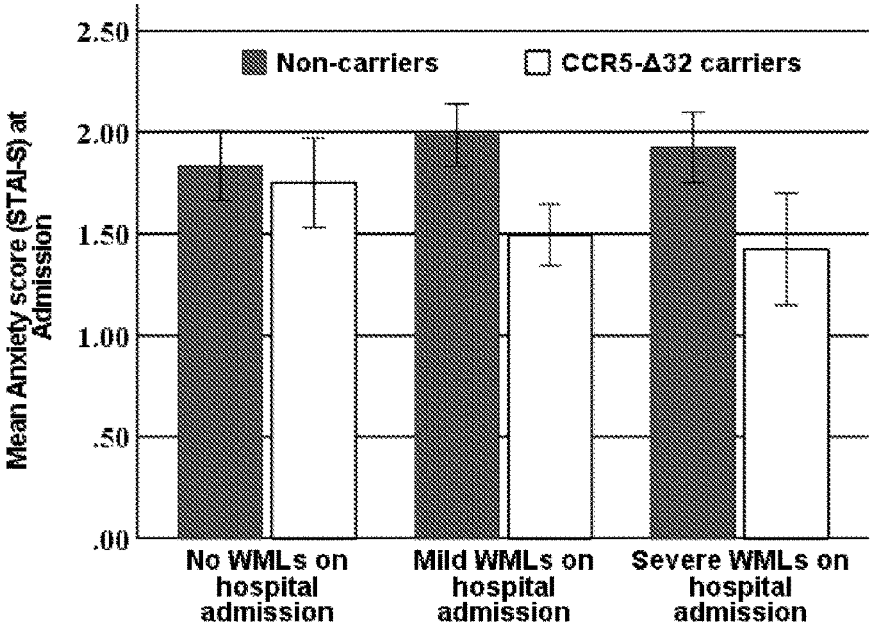

Similar results were obtained for anxiety symptoms developed after hospitalization due to the acute stroke (state anxiety on the state-trait anxiety inventory-severity, STAI-S, such as transitory emotional response to the stressful situation of the acute stroke that involve unpleasant feelings of tension and apprehensive thoughts). FIG. 1C shows that CCR5-Δ32 carriers who did not have WMLs or those who had mild WMLs on hospital admission manifested significantly less current anxiety symptoms than non-carriers who had no WMLs or mild WMLs, respectively. CCR5-Δ32 carriers who had severe WMLs on hospital admission also showed significantly less current anxiety symptoms than the non-carriers having severe WMLs, $p=0.011$ (mean anxiety score according to the STAI-S scale, FIG. 1C).

In the experiments described in FIGS. 1D-1G discussed below, the Post-traumatic stress disorder (PTSD)-Checklist Specific for a stressor (PCL-S), using the stressor "stroke", was used to quantify the level of post-stroke anxiety. The PCL-S is a 17-item scale that corresponds to the DSM-IV criteria for PTSD).

Figure 1D:
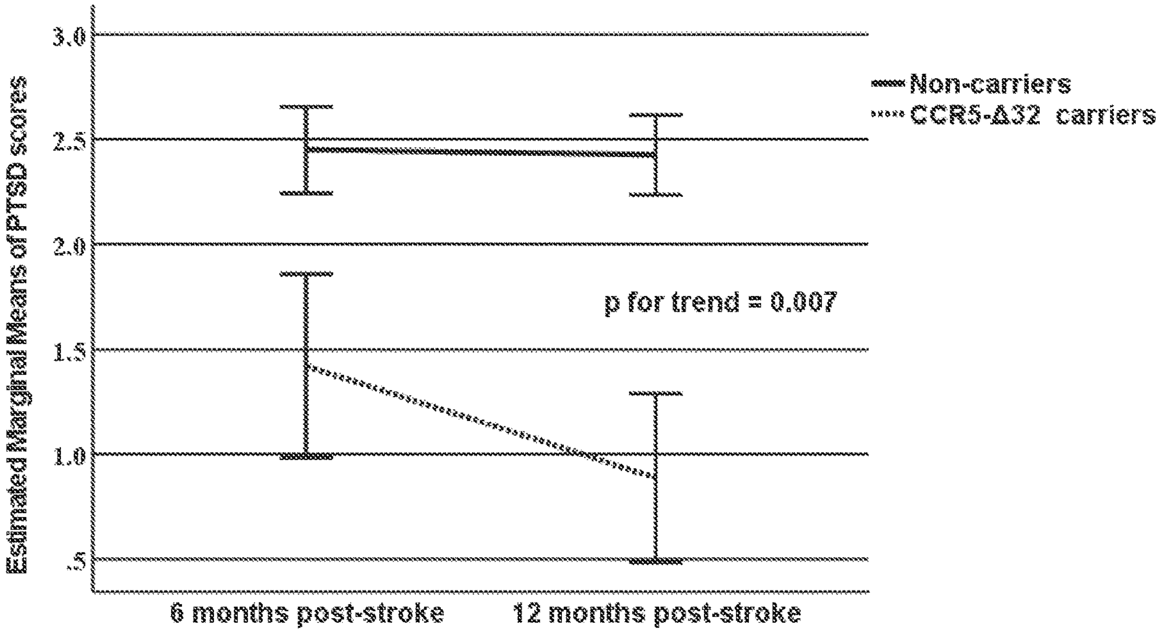
Figure 1E:
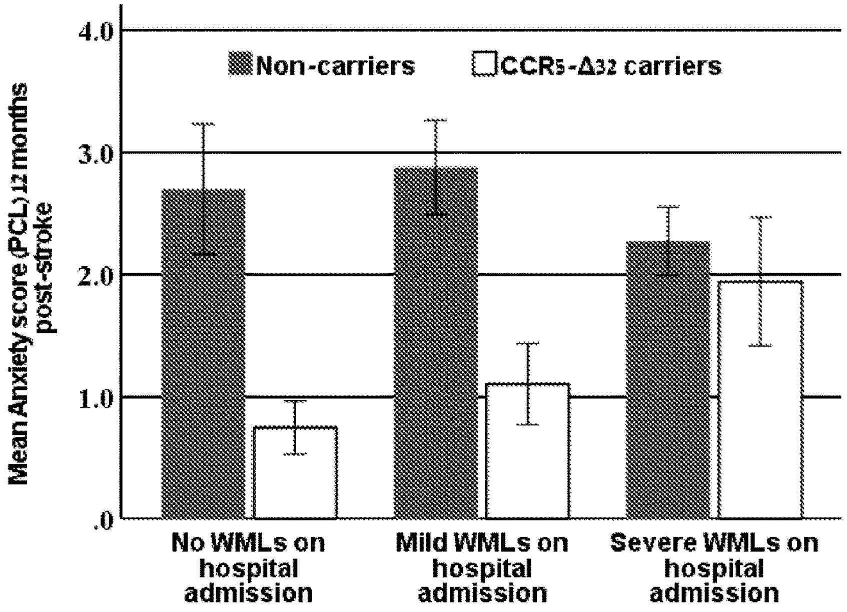
Figure 1F:
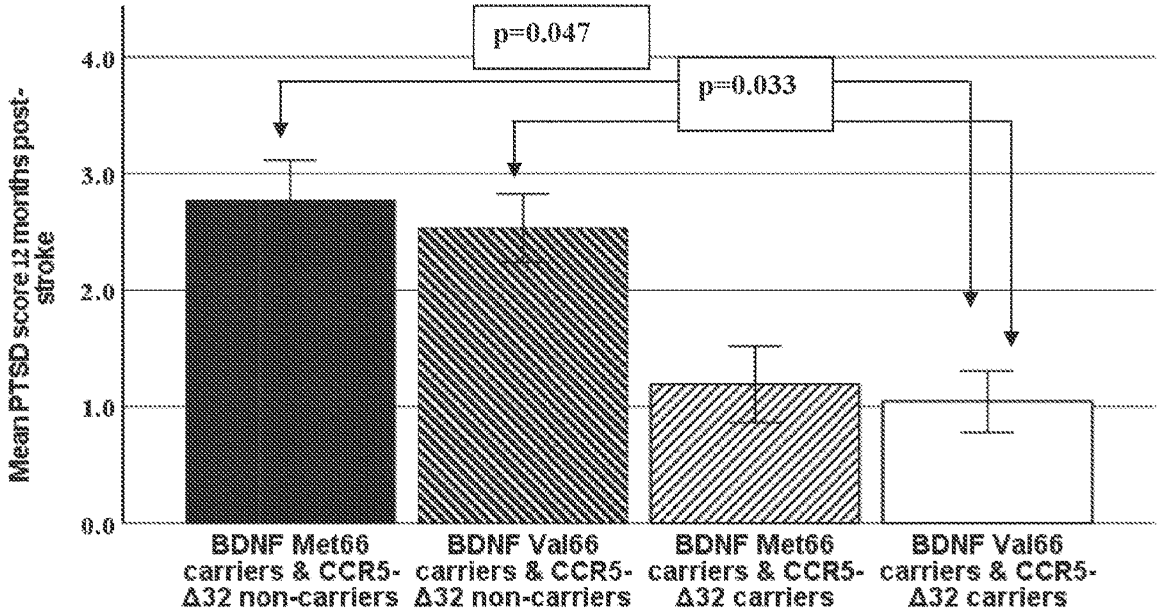

When the anxiety symptoms were evaluated in the post-stroke patients six months or one year after the stroke event, CCR5-Δ32 carriers presented lower anxiety scores compared to non-carriers, as well as less post-traumatic stress symptoms, such as intrusive symptoms (memories, dreams, and flashbacks), persistent avoidance of stroke-associated stimuli, negative alterations in cognition and mood, and increased reactivity, 6 and 12 months after the index event (FIG. 1D). The association of CCR5-Δ32 and anxiety symptoms remained significant after adjustment for age, gender and education. FIG. 1E shows that CCR5-Δ32 carriers who did not have WMLs or those who had mild WMLs on hospital admission manifested one year after stoke significantly less anxiety scores/post-traumatic stress s symptoms than non-carriers who had no WMLs or mild WMLs, respectively. Also, CCR5-Δ32 carriers who had severe WMLs on hospital admission showed one year after stroke less anxiety symptoms than the non-carriers having severe WMLs (FIG. 1E).

Thus, the post-stroke patients carrying the CCR5-Δ32 mutation had significantly less anxiety and depressive symptoms up to 24 months after the index stroke compared to non-carriers.

Figure 1G:
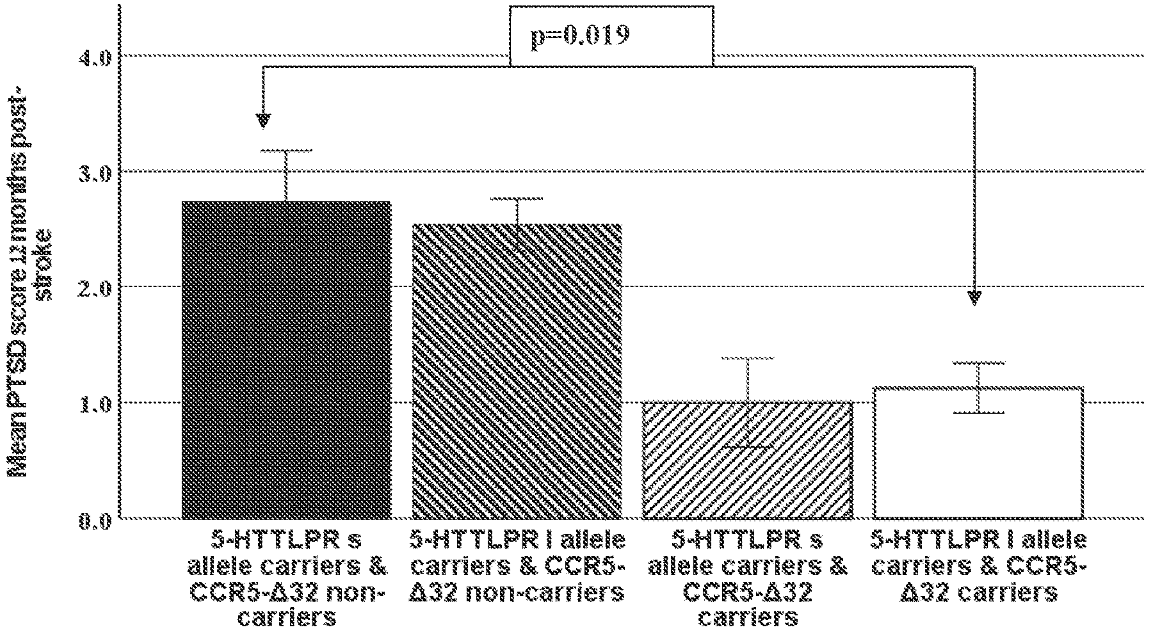
Figure 1H:
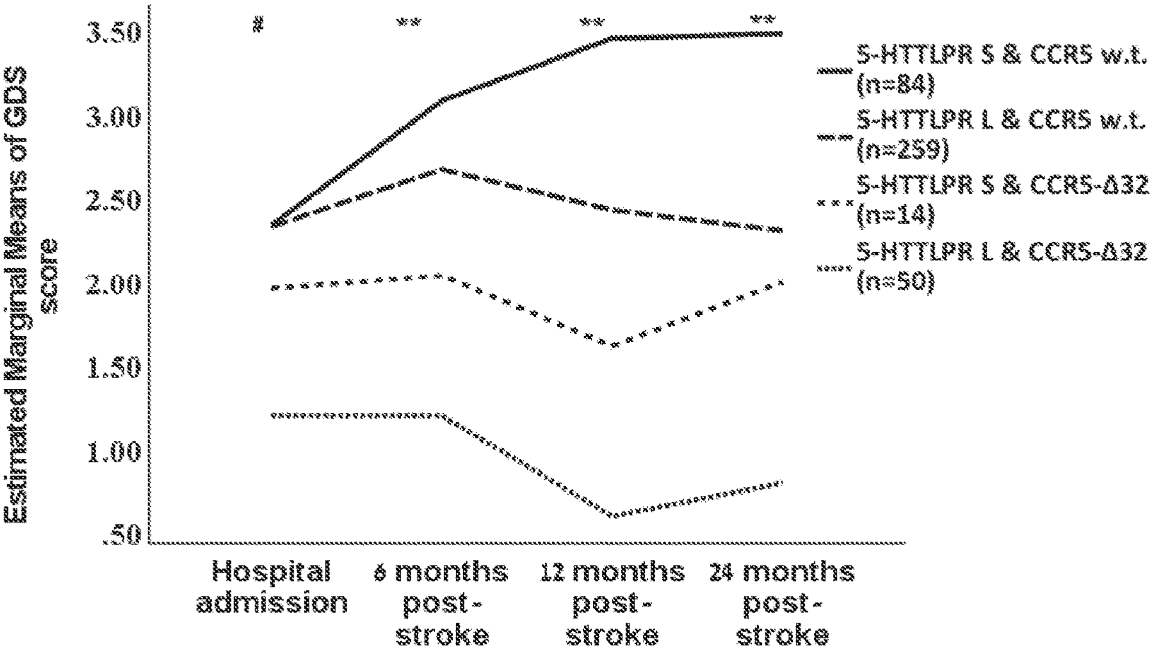

Since the etiology of MDD and anxiety/post-traumatic stress symptoms is greatly influenced by genetic predisposition, the effects of CCR5-Δ32 on post-stroke anxiety scores were compared with two other genetic variants, the Brain-derived neurotrophic factor (BDNF) Met66 allele (FIG. 1F) and the serotonin-transporter-linked polymorphic region (5-HTTLPR; FIG. 1G), each of which has been implicated in the pathophysiology of MDD and stress-related anxiety risk. Surprisingly, the effect of the CCR5-Δ32 genotype on anxiety scores/post-traumatic stress symptoms (PCL-S score) was significantly stronger than the effect of the BDNF (FIG. 1F) or the 5-HTTLR genotypes (FIG. 1G). This was also evident when the effect of the CCR5-Δ32 genotype on depressive symptoms was compared to the effect of 5-HTTLR genotypes using GLM analysis of repeated measures of longitudinal depression scores at admission, 6, 12, and 24 months after stroke (FIG. 1H).

Example 2. White Matter Integrity and Inflammatory Biomarkers

Previous reports showed that stroke-induced disruption of the blood-brain barrier (BBB) is aggravated and prolonged by systemic inflammation, with subsequent damage to the white matter (WM). In order to find out whether CCR5 plays some role in BBB leakage and white matter integrity, fluid-attenuated inversion recovery (FLAIR) images, T1 weighted post contrast images, and Dynamic Contrast Enhanced (DCE) calculated maps of $K^{trans}$ and $K_{ap}$ were performed for two patients from the cohort: a CCR5-Δ32 non-carrier stroke patient with elevated inflammatory markers and a CCR5-Δ32 carrier patient with a normal inflammatory profile.

Figure 2:
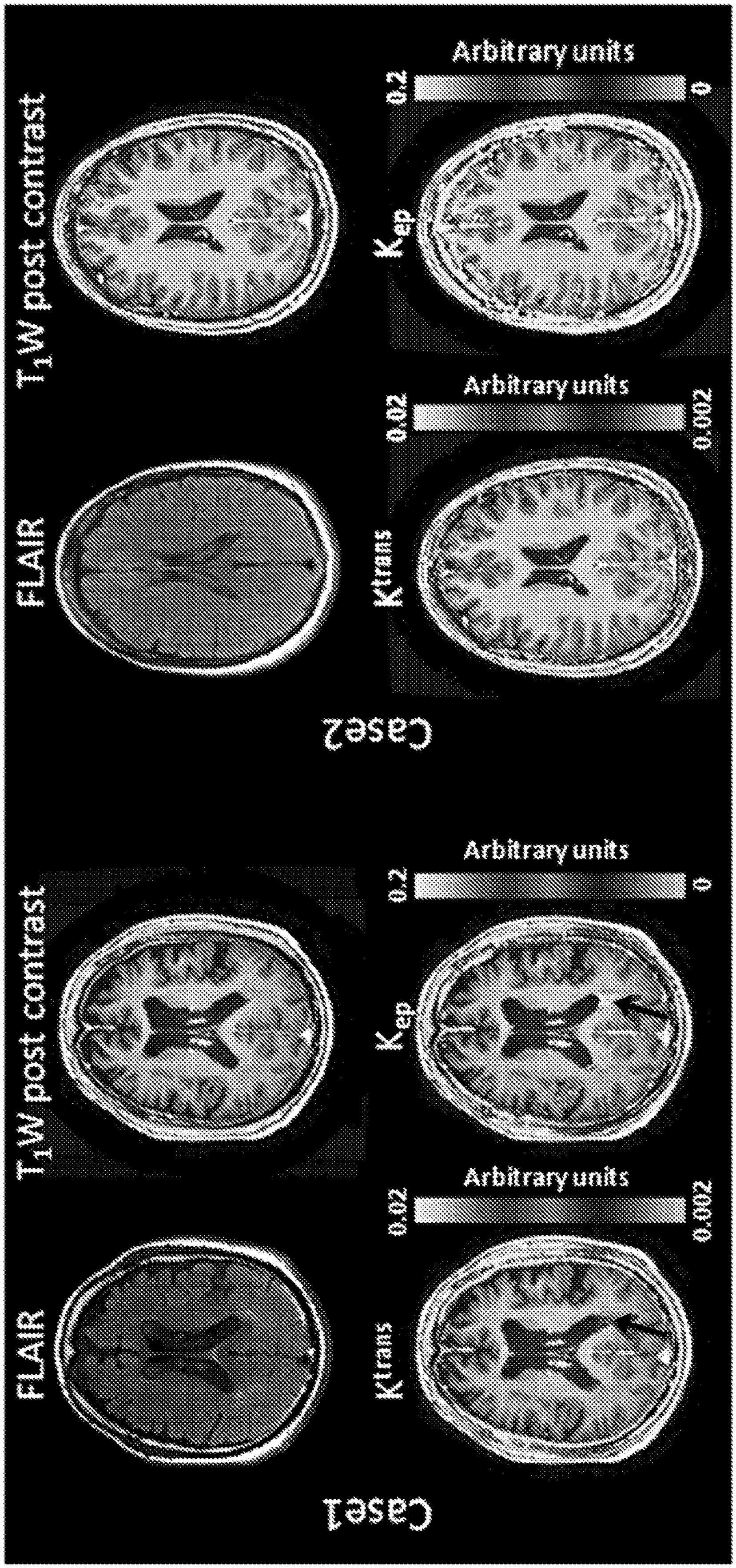
FIG. 2 presents fluid-attenuated inversion recovery (FLAIR), T1 weighted post contrast images and Dynamic Contrast Enhanced (DCE) calculated maps of $K^{trans}$ and $K_{ep}$ of two representative patients: A CCR5-Δ32 non-carrier stroke patient showing regions with increase permeability (BBB leakage, marked with red arrow) around the left lateral ventricle; and a CCR5-Δ32 carrier stroke patient showing no evidence of BBB leakage.

As shown in FIG. 2, while BBB leakage was observed (marked with arrow) around the left lateral ventricle of the CCR5-Δ32 non-carrier patient, a phenomenon consistent with WML, there was no evidence of BBB leakage around the left lateral ventricle of the CCR5-Δ32 carrier.

Determination of the inflammatory molecule C-reactive protein (CRP) in serum of CCR5-Δ32 carriers and CCR5-Δ32 non-carriers indicated that CCR5-Δ32 non-carriers had higher levels of serum CRP on hospital admission compared with carriers of this mutation (p=0.006). Without wishing to be bound by any theory or mechanism of action, CCR5 antagonists may prevent and/or treat the deleterious neuromodulatory reactions associated with elevated inflammation that occur ahead or during depression.

Example 3. Role of CCR5 and White Matter Lesions in Cognitive Impairment

Figure 3:
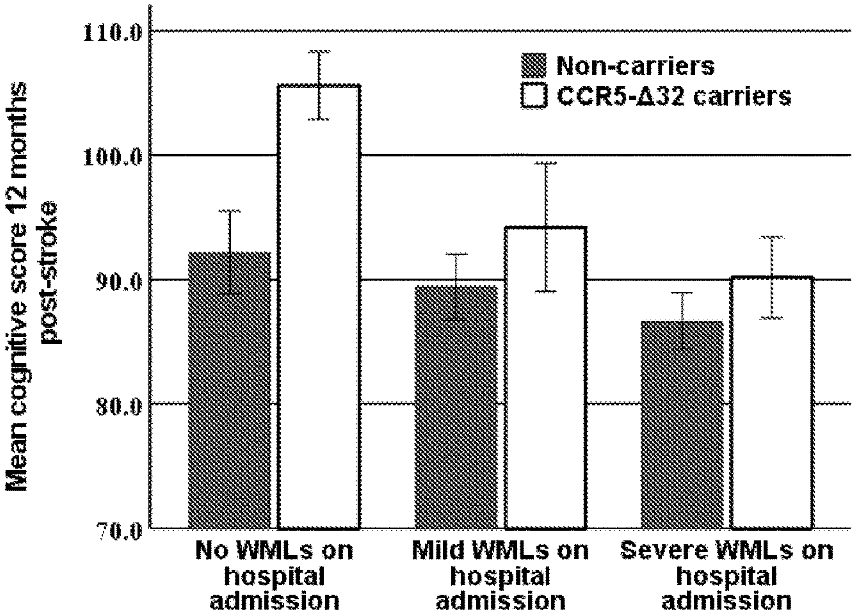
FIG. 3 depicts cognitive performance one year after stroke in CCR5-Δ32 carriers vs. non-carriers categorized by groups of WMLs.

The post-stroke patients of the cohort study, categorized according to their white matter lesions (WMLs) on hospital admission, were then evaluated for their cognitive performance one year after stroke. FIG. 3 shows that CCR5-Δ32 carriers showed better performance in total cognitive scores compared to non-carriers in each of the WMLs groups (FIG. 3; p=0.003).

Example 4. Role of CCR5 in Post-Stroke Depression in Men Vs. Women

Figure 4:
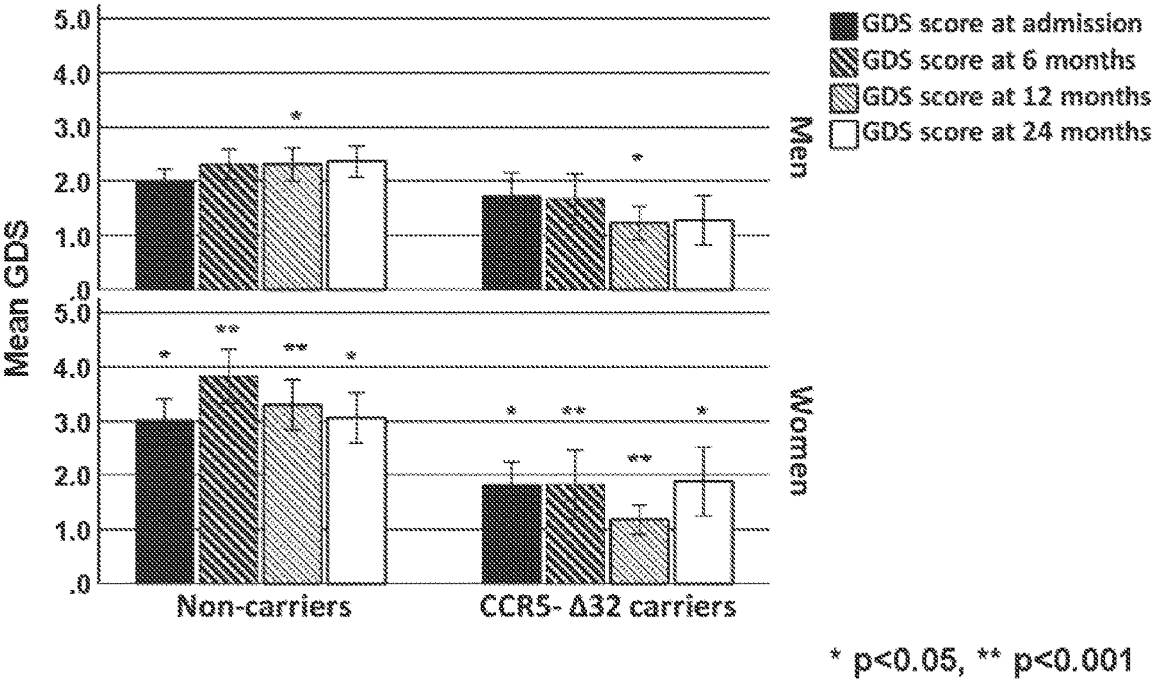
FIG. 4 depicts depression scores at admission, 6, 12 and 24 months after stroke comparing CCR5-Δ32 carriers to non-carriers by sex.

The post-stroke patients of the cohort study were categorized according to sex and the general depressive scores (GDS) were next compared in CCR5-Δ32 carriers vs. non-carriers upon hospital admission as well as 6, 12 and 24 months after the stroke as a function of sex. As shown in FIG. 4, women carrying the CCR5-Δ32 mutation manifested less depressive symptoms than men six months and one year after the stroke event. These results indicate that the protective effect of the CCR5-Δ32 mutation on manifestation of depressive symptoms in stroke patients is more prominent in women than men.

Example 5. CCR5-Δ32 and Major Depressive Disorder (MDD)

A genetic examination of a cohort of MDD patients is performed essentially as described in Example 1. The cohort's subjects are patients with the diagnosis of DSM-IV or DSM-5 Major Depressive Disorder, who have had extensive evaluation of their psychiatric status. The MDD patients are evaluated for genetic distribution of the CCR5-Δ32 mutation compared to control subjects, as described in Example 1.

Example 6. Clinical Study on PSD

A clinical study to evaluate the safety, tolerability and efficacy of maraviroc in patients suffering from post-stroke depression (PSD) was performed as follows:

Ten men and women aged 50 to 86 years who experience stroke, i.e., cerebral infarction or transient ischemic attack (TIA) prior to the initiation of the study were enrolled to the study. These subjects also experienced a major depressive episode that develops within 12 months from the stroke/TIA. Clinical diagnosis of stroke was performed according to the World Health Organization Monica Project. Subjects exhibited evidence of ischemic infarct and/or lacunar infarcts on MM (defined as sharply demarcated hypointense lesions <20 mm on T1-weighted images with corresponding hypointense lesions with hyperintense rim on FLAIR) and/or deep Cerebral Microbleeds (CMB) (defined as round hypointense lesions on T2-weighted gradient echo-images with a diameter <10 mm in neuroimaging. Clinical diagnosis of a major depressive episode was performed according to the Diagnostic and Statistical Manual of Mental Disorders-$5^{th}$ edition (DSM-5)—diagnostic criteria. The subjects had an Inventory of Depressive Symptomatology 30-item Clinician-rated (IDS-C30) total score ≥34 at pre-dose at Day 1.

Exclusion criteria comprise e.g. 1) significant acute neurologic illness including: impaired consciousness, Parkinson's disease, Huntington's chorea, progressive supranuclear paralysis, brain tumor, subdural hematoma, multiple sclerosis, hydrocephalus, Binswanger's disease, or severe aphasia, 2) patients diagnosed with dementia or significant cognitive impairment as defined by a MoCA score <20 at screening, or other neurological conditions (multiple sclerosis, Parkinson's disease, epilepsy, Huntington's chorea, brain tumor, subdural hematoma, multiple sclerosis, hydrocephalus, or Binswanger's disease), 3) positive serology for Hepatitis B or C; or for HIV.

Each subject received 300 mg maraviroc daily or 150 mg daily for 10 weeks. Post-treatment follow-up was conducted for 8 weeks after the last dose of Maraviroc. During the 10 weeks of maraviroc treatment the subjects were evaluated every two weeks, and during the 8 weeks of follow-up the subjects were evaluated at the $4^{th}$ and $8^{th}$ week after the last dose of maraviroc.

The subjects were evaluated for the efficacy of maraviroc by assessing the improvement in depressive symptoms determined by a change from baseline (i.e., Day 1 pre-dose) in the Montgomery-Asberg Depression Rating Scale (MADRS) total score. Other assessments included, for example, assessment of depressive symptoms by the 16-item Quick Inventory of Depressive Symptomatology-Self Report (QIDS-SR16); assessment of remission, defined as a MADRS total score ≤10; assessment of response, defined as a ≥50% reduction from baseline in MADRS total score; evaluation of symptoms of anxiety as assessed by the Generalized Anxiety Disorder 7-item Scale (GAD-7)—each item is rated on a 4-point scale (0 to 3), with the total score range from 0-21 (higher scores indicating more anxiety); and evaluation of cognitive status, as assessed by cognitive score based on repeatable computerized battery of cognitive tests (Neurotrax) and Montreal Cognitive Assessment (MoCA).

Additional assessments include e.g. the clinical global impression-improvement (CGI-I), a 7 point scale that requires the clinician to assess how much the patient's illness has improved or worsened relative to a baseline state at the beginning of the intervention; the clinical global impression-severity (CGI-S), which evaluates the severity of psychopathology from 1 to 7, and provides an overall clinician-determined summary measure that takes into account all available information, including knowledge of the subject's history, psychosocial circumstances, symptoms, behavior, and the impact of the symptoms on the subject's ability to function; Patient Global Impression scales, commonly used measures of symptom severity, treatment response and the efficacy of treatments; the patient global impression-severity (PGI-S), that provides an overall patient-rated summary measure that assesses the severity of the subject's MDD; the patient global impression of change (PGI-C) which provides an overall patient-rated summary that assesses subject perception of change in their MDD since starting study treatment; the EuroQol Group; 5 dimension (EQ-5D) which is a standardized 2-part instrument for use as a measure of health outcome, primarily designed for self-completion by respondents. The EuroQol Group; 5 dimension; 5 level (EQ-5D-5L) descriptive system comprises the following 5 dimensions: mobility, self-care, usual activities, pain/discomfort and anxiety/depression. Each dimension has 5 levels: no problems, slight problems, moderate problems, severe problems, and extreme problems; the EQ visual analog scale (EQ-VAS) self-rating records the respondent's own assessment of their health status; SIS—stroke impact scale; Quality of life enjoyment and satisfaction questionnaire; ADL—the activities of daily living score; and RNL—Reintegration to Normal Living Index.

The study also includes assessment of the safety and tolerability of the drug by evaluating its effects on heart rate, blood pressure and on suicidal ideation/behavior measured by the Columbia Suicide Severity Rating Scale (C-SSRS). Additional assessments include evaluation of the effects of the drug on blood inflammatory markers and on MRI measures to evaluate WML. MRI analyses included assessment of white matter (WM) hyperintensities, tissue segmentation and Brain atrophy measures.

maraviroc was given as an add-on therapy to the subject's usual prescribed antidepressant. However, if no antidepressant was given to the subject at the time of enrollment, maraviroc was given as a sole treatment.

Several patients have already received daily administration of 300 mg maraviroc (once-daily oral administration) by the time of data collection, as detailed below:

Patient 1—Age 54 years, male. Medical history: hypertension, diabetes mellitus, hyperlipidemia. The patient had a history of persistent depressive symptoms and anxiety 10 years before the stroke (m/p dysthymia), which was treated with escitalopram with partial improvement. Stroke history: left MCA occlusion 4 months prior to study entrance. WML load (Fazekas score): 1, no cognitive impairment. Shortly after the stroke, the patient's depressive symptoms markedly worsened, amounting to a newly diagnosed major depressive event. He was treated with the SSRI escitalopram, either alone or in combination with mirtazapine, with no improvement. The patient completed 10 weeks of treatment by the time of data collection.

Patient 2—Age 56 years, male. Medical history: hypertension, diabetes mellitus, hyperlipidemia, renal cell carcinoma. Stroke history: 2 events, 1 lacunar infarct in midbrain and right thalamus with left side weakness and dysarthria 15 months prior to study entrance; the second was a month later with left parietal subarachnoid hemorrhagic lesions. WML load: 1. In addition, mild signs of cognitive impairment were observed in the patient after the stroke. The patient developed major depression and treated with the SSRI agent escitalopram, either alone or in combination with pregabalin (a drug having GABA antagonist activity, exerting inter alia anti-anxiety activity), with no improvement. The patient completed 10 weeks of treatment by the time of data collection.

Patient 3—Age 67 years, female. Medical history: hypertension, hyperglycemia, hyperlipidemia, past smoking, s/p bariatric surgery. Stroke history: right parietal infarct with left side weakness, dysarthria and hemianopia 3 years prior to study entrance. WML load: 3. In addition, mild signs of cognitive impairment were observed in the patient after the stroke. The patient developed depression and anxiety about one year after the event, and was treated with the SSRI agent escitalopram, either alone or in combination with sertraline and psychotherapy, with no improvement. Patient was also prescribed pregabalin. The patient completed 7 weeks of treatment by the time of data collection.

Patient 4—Age 60 years, male. Medical history: hypertension, smoking. Stroke history: occipital lesions from both sides and proximal basilar stenosis with left side weakness and confusion 6 months prior to study entrance. WML load: 1. In addition, mild signs of cognitive impairment were observed in the patient after the stroke. The patient developed depression first time in his life after the event. The patient completed 4 weeks of treatment by the time of data collection.

In summary, all patients were diagnosed with major post-stroke depression (PSD) with both depressive and anxiety symptoms. Patients 1 and 3, diagnosed with treatment-resistant depression (TRD), and patient 2, exhibiting resistance to escitalopram, received maraviroc as an add-on combination therapy. Patient 4 received maraviroc as first-line monotherapy.

Side effects reported by the participants during the study: 1 transient impotence, 1 severe constipation (drug-unrelated). Results of the efficacy evaluation are presented in FIGS. 5-6.

Figure 5:
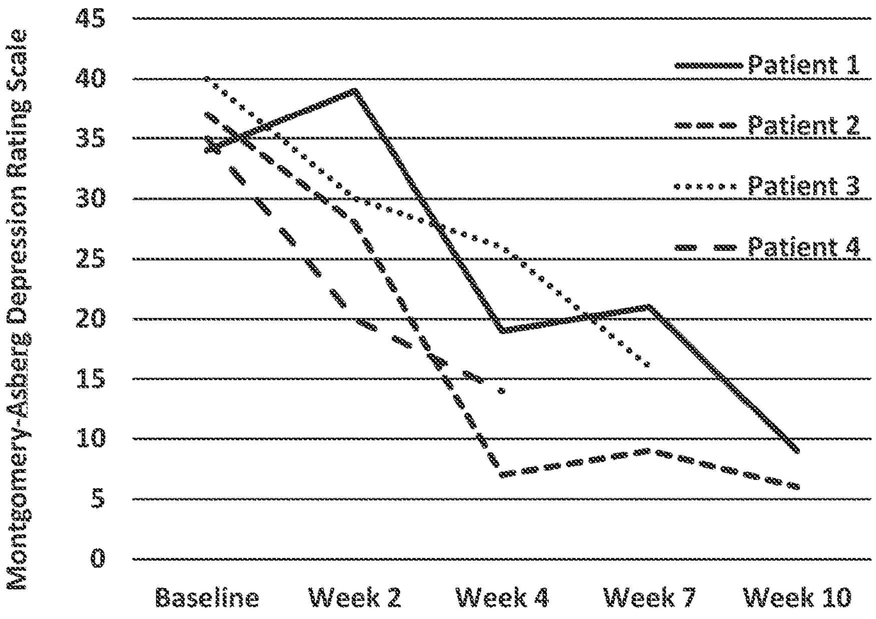
FIG. 5 depicts depression scores in 4 patients treated with maraviroc 300 mg daily, as assessed by a senior psychiatrist.

FIG. 5 presents the depressive scores of the patients enrolled in the study, as evaluated by a senior psychiatrist. For all patients, treatment effects began within a remarkably short time period of between 1-2 weeks from first dose of maraviroc. Further, all patients improved their depressive symptoms, as measured by lower depressive scores on the Montgomery Asberg Depression Rating Scale (MADRS)—as can be seen in FIG. 5, the severe initial scores of about 35-40 were markedly reduced to scores of MADRS <20, and, depending on treatment duration, up to about 5-10 following 10 weeks of treatment.

Figure 6:
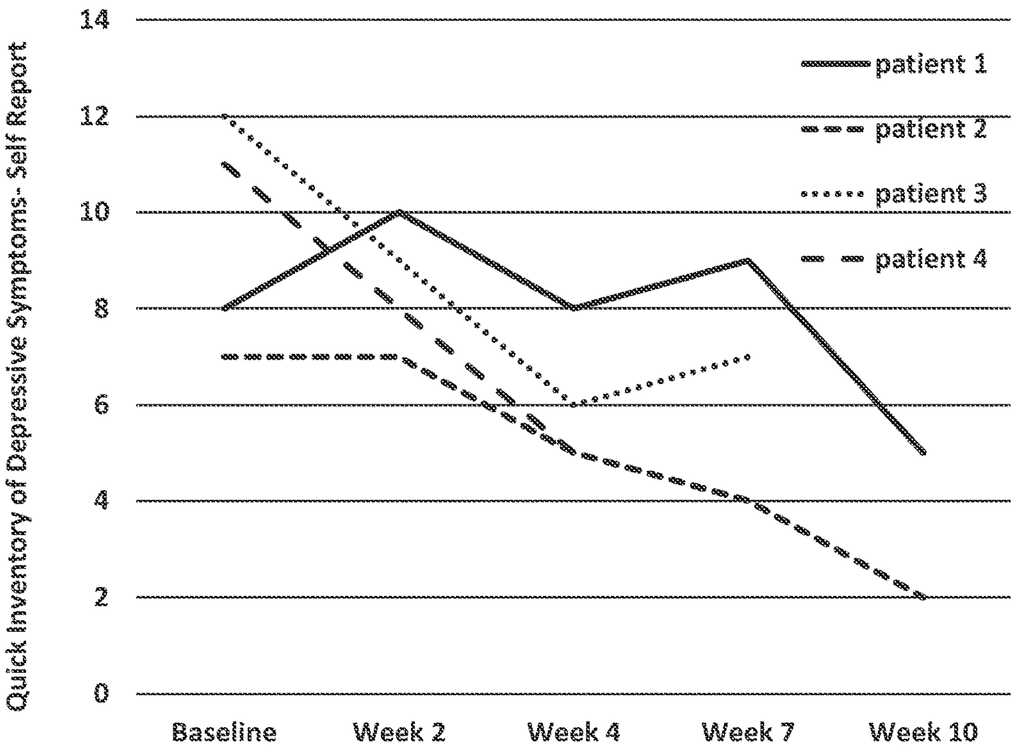
FIG. 6 depicts depression scores in 4 patients treated with maraviroc 300 mg daily, as assessed by the patient.

As can be seen in FIG. 6, these findings were further validated by self-report depressive scores, as evaluated by the patients. For all patients, self-reported treatment effect began between 1-2 weeks from first dose of maraviroc. All patients improved their depressive symptoms, as measured by lower depressive scores on the quick inventory of depressive symptoms-self report (QIDS-SR). In addition, the improvement was also apparent as reduction in the patients' CGI-S scores as determined by the psychiatrist at admission and by data collection. In all participants, CGI=5 scores (markedly ill) were determined upon admission. Remarkably, in all patients who completed at least 7 weeks of treatment (patients 1-3), the CGI severity upon data collection ranged between 3 (mildly ill) to 2 (borderline mentally ill). Patient 4 was determined as CGI=3 (mildly ill) after only four weeks of treatment.

Further, as can be seen in Table 2 below, maraviroc was also effective in reducing anxiety symptoms. In particular, major improvements in anxiety scores were observed in subjects initially exhibiting moderate or severe anxiety (GAD-7 of 10-14 and 15-21, respectively) upon admission.

TABLE 2

| Anxiety scores (GAD-7 severity) | | |
|---|---|---|
| Patient | GAD-7 at admission | GAD-7 at data collection |
| Patient 1 | 17 (severe) | 10 (moderate) |
| Patient 2 | 6 (mild) | 6 (mild) |
| Patient 3 | 8 (mild) | 7 (mild*) |
| Patient 4 | 14 (moderate) | 8 (mild*) |

*patient completed less than 10 weeks of treatment at the time of data collection - score was determined at week 7 in patient 3 and at week 4 for patient 4.

Thus, maraviroc was found to be remarkably effective in the inhibition and reversal of depressive and anxiety symptoms. An extraordinarily short time to response was reported, as opposed to a typical response time of 4-6 weeks for SSRI and SNRI. Further, all patients exhibited a marked reduction in depression scores, in all evaluation scales used for assessment. For example, the patients' depression scores were reduced from a range of MADRS >34 (severe MDD) to MADRS <20 (mild depression), or even <7 (normal/symptom-absent). In other words, a highly significant reduction of 60% to 80% in depressive scores and even remission was obtained in the treated patients within an unusually short period of time. The effects were manifested for both combination therapy with maraviroc and for maraviroc when used as a sole active ingredient.

Accordingly, maraviroc was unexpectedly found to be particularly effective in the treatment of MDD, in particular of post-stroke depression and anxiety in human subjects, including in TRD patients.

Example 7. Clinical Study on PSCI

A randomized, triple-blind, placebo-controlled clinical trial is performed, of maraviroc 150 mg or 600 mg per day compared to placebo administered for 12 months in patients diagnosed with recent (1-24 months) subcortical stroke who experience mild post-stroke cognitive impairment (PSCI) and have evidence of white matter lesions (WMLs) and small vessel disease (SVD) on neuroimaging.

Men and women aged 50 to 86 years are enrolled for the trial, who fulfill the diagnostic criteria for PSCI/subcortical vascular cognitive impairment, that developed after the documented stroke/TIA, as outlined by Skrobot and colleagues. This requires the presence of a cognitive syndrome (as defined in Section A below) and SVD. Impairment in at least one cognitive domain and mild to no impairment in instrumental activities of daily living (IADLs)/activities of daily living (ADLs), respectively (independent of the motor/sensory sequelae of the vascular event); A. Cognitive Syndrome defined as: 1. Dysexecutive Syndrome: Some impairment in goal formulation, initiation, planning, organizing, sequencing, executing, set-shifting and maintenance, or abstracting; 2. Memory Deficit: Some impairment in recall, relative intact recognition, less severe forgetting, benefit from cues. B. Small Vessel Ischaemic Disease defined as: 1. Evidence of relevant cerebrovascular disease by brain imaging (in the last 24 months) defined as the presence of both: (i) Periventricular and deep WMLs (grading scale >1 on the Fazekas score) plus at least one lacunar infarct; and (ii) Absence of cortical and/or cortico-subcortical non-lacunar territorial infarcts and watershed infarcts, indicating large vessel disease, signs of normal pressure hydrocephalus, or other specific causes of WML. Presence or a history of neurological signs as evidence for cerebrovascular disease, and mild symptomatology of cognitive impairment, as defined by a screening Montreal Cognitive Assessment (MoCA) score less than 27 and CDR of 0.0 or 0.5, are additional exemplary inclusion criteria.

Exclusion criteria are e.g. with dementia or significant cognitive impairment as defined by a MoCA score <17 at screening and clinical evaluation excluding diagnosis of dementia, or other neurological conditions (multiple sclerosis, Parkinson's disease, epilepsy, etc.) that affects cognition and mobility; hemorrhages and cerebral edema (e.g., subarachnoid haemorrhage, intracerebral hemorrhage, subdural hematoma, epidural hematoma); patients in a state of coma or with severe disturbance of consciousness, aphasia, agnosia, or deafness that subsequently affects expression and communication; significant acute medical illness including: drug overdose, severely disturbed liver, kidney or lung function, anemia, hypothyroidism, or uncontrolled diabetes; presence of cortical involvement on neurologic examination including aphasia; previous diagnosis of a genetic cause of VCI (e.g., CADASIL); history of hepatitis or elevated hepatic transaminases or bilirubin; positive serology for Hepatitis B or C; positive serology for HIV; current or past diagnosis of bipolar or related disorders, intellectual disability, or cluster b personality disorder (e.g., borderline personality disorder, antisocial personality disorder, histrionic personality disorder, and narcissistic personality disorder), psychotic disorder, schizophrenia, obsessive-compulsive disorder, and substance/alcohol use disorders other than nicotine in the past year (including barbiturates, methadone, opiates, cocaine, cannabinoids, and amphetamine/methamphetamine); and suicidal ideation with intent to act during screening phase or on Day 1, or a history of suicidal behavior within the past year.

Eligible patients enrolled in the study undergo a baseline visit (Week 1), in which they receive the study drug following completion of all relevant assessments. Patients are randomly assigned to 48 weeks of treatment with either 150 mg/day maraviroc, 600 mg/day or placebo (control group). Patients assigned to the 600 mg/day group start with 150 mg/day for two weeks, which is escalated to 600 mg/day for the next 46 weeks. Patients are evaluated every 2-12 weeks during the trial using multiple cognitive tests and questionnaires. A final efficacy assessment is held after the patient's last dose (Week 48) and a final safety assessment is held 4 weeks after the patient's last dose (Week 52).

The patients undergo two 3 Tesla brain MRI examinations at Baseline (Week 1) and at study completion (between Week 48-52). The MRI protocol consist of previously described pulse sequences. All axial slices are prescribed on the same orientation, covering the whole brain, aligned along the fourth ventricle-orbitofrontal orientation. MRI analyses include assessment of: (1) Cerebral SVD burden, in accordance with STRIVE score. This score determines: chronic lacunar infarcts, white matter (WM) hyperintensities (graded using the Fazekas score), cerebral microbleeds (CMB) and enlarged perivascular spaces (PVS). (2) Tissue segmentation and Brain atrophy measures. (3) Characterization of microstructural integrity—calculation of the diffusion tensor imaging (DTI) maps in major WM fiber tracts.

The subjects are evaluated for the effects of maraviroc as follows. To investigate the safety and tolerability of maraviroc 150 mg and 600 mg per day vs. placebo in patients with recent subcortical stroke who experience mild PSCI, adverse events (AEs) related to the medication assignment, to rehabilitation practice or to other causes are adjudicated by the Safety Committee with input from the PI. Nature, frequency, severity, and timing of AEs and serious AEs, Physical and neurologic examinations, vital signs, blood tests and electrocardiograms (ECGs), are recorded. AEs of special interest are e.g. blood analyses of liver function, renal function, specifically elevation of hepatic transaminases or bilirubin; elevation of serum creatinine.

Efficacy assessments are performed to evaluate the efficacy of maraviroc 150 mg and 600 mg per day compared with placebo on progression/improvement of clinical symptoms of post-stroke dementia. To evaluate the efficacy of maraviroc 150 mg and 600 mg compared with placebo on change over time from baseline to Month 12 in composite data derived from dementia assessment cognitive scores, the Clinical Dementia Rating-Sum of Boxes (CDR-SB), the Toronto cognitive assessment (TorCA), the global cognitive score based on repeatable computerized battery of cognitive tests (Neurotrax) and the Montreal Cognitive Assessment (MoCA), are used. A negative effect size of cognitive changes represents an improvement in consistency of cognitive symptoms across the included cognition metrics.

Additional efficacy assessments are performed e.g. to evaluate the efficacy of maraviroc 150 mg and 600 mg compared with placebo on function using other measures such as change from baseline to Month 12 on functional scores as assessed by the stroke impact scale (SIS), activities of daily living (ADL) score, gait and balance scores and mean change in functional measures, Reintegration to Normal Living Index (RNL); all-cause discontinuation, subsequent cardiovascular events; change from baseline to Month 12 on behavior assessed by the Center for Epidemiologic Studies-Depression (CES-D), Geriatric depression scale (GDS) and the General Anxiety Disorder-7 (GAD-7) score.

Additional assessments evaluate the effect of treatment vs. placebo on markers of disease over time. Neuroimaging biomarkers: Change from baseline to Month 12 in MM-derived measurements such as volumetric changes in whole brain, ventricles, hippocampus, white matter volume, integrity and connectivity, and locations and number of cerebrovascular lesions, lacunes, microbleeds, or other structures. Blood/plasma biomarker: Mean change in blood biomarkers from baseline over time (Baseline, W2, W12, W24, W48): inflammatory and endothelial function profile, CCR5 ligands (MIP-1α, RANTES), as well as Aβ1-42, t-tau, p-tau 181 (biochemical signature of neurodegeneration). Cerebrospinal fluid (CSF) biomarkers: CSF biomarkers in each arm compared with placebo at W24): cytokines, Aβ1-42, t-tau, p-tau 181 and S100β (a biochemical marker of inflammation that indicates astrocyte activation). Measures of carotid atherosclerosis: assessed by carotid Doppler peak systolic velocity and carotid intima media thickness.

The foregoing description of the specific embodiments will so fully reveal the general nature of the invention that others can, by applying current knowledge, readily modify and/or adapt for various applications such specific embodiments without undue experimentation and without departing from the generic concept, and, therefore, such adaptations and modifications should and are intended to be comprehended within the meaning and range of equivalents of the disclosed embodiments. It is to be understood that the phraseology or terminology employed herein is for the purpose of description and not of limitation. The means, materials, and steps for carrying out various disclosed functions may take a variety of alternative forms without departing from the invention.

The invention claimed is:

1. A method of treating or inhibiting the symptoms of a depressive and/or anxiety disorder selected from the group consisting of post-stroke depression (PSD), post-stroke anxiety (PSA), treatment resistant depression (TRD), and major depressive disorder (MDD), in a subject diagnosed with a cerebral infarction or a transient ischemic attack for 4-24 months, the method comprising administering to the subject a pharmaceutical composition comprising a therapeutically effective amount of maraviroc or a derivative thereof.

2. The method of claim 1, wherein the therapeutically effective amount of maraviroc is 100 mg per day to 300 mg per day, and the subject manifests both depressive and anxiety symptoms.

3. The method of claim 1, wherein the subject is at high risk of suicidal behavior evaluated by the Columbia Suicide Severity Rating Scale (C-SSRS); the subject is a human female; or wherein said subject is over 50 years of age or over 65 years of age.

4. The method of claim 1, wherein the subject is diagnosed as being afflicted with post-stroke depression and/or post-stroke anxiety.

5. The method of claim 4, wherein said subject is further diagnosed with post-stroke cognitive impairment (PSCI); or said subject is diagnosed with mild to moderate white matter lesions (WMLs) load or with severe WML load as evaluated by the Fazekas score prior to treatment.

6. The method according to claim 1, comprising administering to said subject maraviroc in concurrent or sequential combination with at least one antidepressant selected from the group consisting of a selective serotonin reuptake inhibitor (SSRI) and a serotonin-norepinephrine reuptake inhibitor (SNRI).

7. The method according to claim 1, comprising administering to said subject maraviroc as a sole active ingredient.

8. A method for treating treatment-resistant depression (TRD) in a human subject in need thereof, comprising administering to the subject a pharmaceutical composition comprising a therapeutically effective amount of a CCR5 inhibitor or antagonist, wherein the CCR5 inhibitor is maraviroc or a derivative thereof.

9. The method of claim 8, comprising administering to said subject maraviroc in concurrent or sequential combination with at least one antidepressant selected from the group consisting of a selective serotonin reuptake inhibitor (SSRI) and a Serotonin-Norepinephrine Reuptake Inhibitor (SNRI).

10. The method of claim 8, wherein said subject is resistant to treatment with at least one of citalopram, escitalopram, sertraline, mirtazapine, and combinations thereof, or the subject is at high risk of suicidal behavior evaluated by the Columbia Suicide Severity Rating Scale (C-SSRS).

11. The method of claim 8, comprising administering to said subject maraviroc in combination with citalopram, escitalopram, sertraline, mirtazapine, or combinations thereof; or administering to said subject maraviroc as a sole active ingredient.

12. A method of treating post-stroke cognitive impairment (PSCI) in a subject diagnosed with established PSCI, comprising administering to the subject Maraviroc in a therapeutically effective amount of 100 mg per day to 600 mg per day, wherein treating comprises improving the cognitive impairment of the subject characterized by an improved cognitive score of at least two points compared to the score determined prior to treatment.

13. The method of claim 12, wherein treating said subject has been diagnosed with cerebral infarction or transient ischemic attack 4-24 months prior to administration of the maraviroc.

14. The method of claim 12, wherein treating comprises eliminating or reducing the severity of a symptom or clinical sign associated with PSCI compared to its level as determined prior to treatment.

15. The method of claim 12, wherein the subject is further diagnosed with depression and/or anxiety within one month to two years of stroke occurrence.

16. The method of claim 12, wherein said subject is diagnosed with white matter lesions (WMLs) prior to treatment, wherein said subject is diagnosed with mild to moderate WML load or with severe WML load as evaluated by the Fazekas score.

17. The method of claim 12, wherein the improvement in cognitive score is assessed using the Toronto Cognitive Assessment (TorCA) test.

* * * * *